(12) United States Patent
Adams et al.

(10) Patent No.: US 11,801,055 B2
(45) Date of Patent: *Oct. 31, 2023

(54) METHOD FOR CONTROLLING END EFFECTOR CLOSURE FOR POWERED SURGICAL STAPLER

(71) Applicant: Cilag GmbH International, Zug (CH)

(72) Inventors: Shane R. Adams, Lebanon, OH (US); Thomas E. Adams, Loveland, OH (US); Nicholas J. Ross, Franklin, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 61 days.

This patent is subject to a terminal disclaimer.

(21) Appl. No.: 17/464,797

(22) Filed: Sep. 2, 2021

(65) Prior Publication Data

US 2022/0039799 A1 Feb. 10, 2022

Related U.S. Application Data

(63) Continuation of application No. 16/574,281, filed on Sep. 18, 2019, now Pat. No. 11,185,331.

(51) Int. Cl.
*A61B 17/115* (2006.01)
*A61B 17/072* (2006.01)
(Continued)

(52) U.S. Cl.
CPC .... *A61B 17/1155* (2013.01); *A61B 17/07207* (2013.01); *A61B 17/1114* (2013.01);
(Continued)

(58) Field of Classification Search
CPC .......... A61B 17/1155; A61B 17/07207; A61B 17/1114
See application file for complete search history.

(56) References Cited

U.S. PATENT DOCUMENTS 5,205,459 A  4/1993  Brinkerhoff et al.
5,271,544 A  12/1993  Fox et al.
(Continued)

FOREIGN PATENT DOCUMENTS

EP  2992841 A2  3/2016
EP  3412225 A1  12/2018
(Continued)

OTHER PUBLICATIONS

European Search Report, Extended, and Written Opinion dated Nov. 9, 2020, for Application No. 20196684.3, 13 pages.
(Continued)

*Primary Examiner* — Nathaniel C Chukwurah
(74) *Attorney, Agent, or Firm* — Frost Brown Todd LLP

(57) ABSTRACT

A powered surgical stapler includes a motor unit, a movable member, a controller, a sensor assembly, an anvil, and an opposing deck surface. A method of operating the stapler includes controlling the motor unit to actuate the movable member to move from the open position towards the closed position. The method also includes sensing closure data using the sensor assembly. The closure data includes an initial tissue contact position, a gap formed between the anvil and the opposing deck surface, and an axial force on the anvil. The method also includes communicating the closure data to the controller. The method also includes determining at least one of an adjusted closure rate or an adjusted closure stroke using the closure data. The method also includes controlling the motor unit using at least one of the adjusted closure rate or the adjusted closure stroke.

20 Claims, 19 Drawing Sheets

(51) Int. Cl.
    *A61B 17/11*      (2006.01)
    *A61B 17/00*      (2006.01)
(52) U.S. Cl.
    CPC ............... *A61B 2017/00398* (2013.01); *A61B 2017/00477* (2013.01); *A61B 2017/00734* (2013.01); *A61B 2017/07257* (2013.01); *A61B 2017/1132* (2013.01); *A61B 2017/1135* (2013.01); *A61B 2017/1139* (2013.01)

(56) References Cited

U.S. PATENT DOCUMENTS

| | | |
|---|---|---|
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,350,104 A | 9/1994 | Main et al. |
| 5,533,661 A | 7/1996 | Main et al. |
| 8,028,885 B2 | 10/2011 | Smith et al. |
| 8,910,847 B2 | 12/2014 | Nalagatla et al. |
| 9,445,816 B2 | 9/2016 | Swayze et al. |
| 9,463,022 B2 | 10/2016 | Swayze et al. |
| 9,532,783 B2 | 1/2017 | Swayze et al. |
| 9,597,081 B2 | 3/2017 | Swayze et al. |
| 9,808,307 B2 | 11/2017 | Trees et al. |
| 10,045,780 B2 | 8/2018 | Adams et al. |
| 10,307,157 B2 | 6/2019 | Miller et al. |
| 11,123,074 B2 | 9/2021 | Adams et al. |
| 11,185,324 B2 | 11/2021 | Adams et al. |
| 11,185,331 B2* | 11/2021 | Adams ................ A61B 17/1114 |
| 11,464,516 B2 | 10/2022 | Adams et al. |
| 2015/0083772 A1 | 3/2015 | Miller et al. |
| 2015/0083773 A1 | 3/2015 | Measamer et al. |
| 2015/0083774 A1 | 3/2015 | Measamer et al. |
| 2015/0083775 A1 | 3/2015 | Leimbach et al. |
| 2017/0258471 A1* | 9/2017 | DiNardo ............ A61B 17/1155 |
| 2018/0325517 A1* | 11/2018 | Wingardner ....... A61B 17/1155 |
| 2018/0368836 A1 | 12/2018 | Auld et al. |

FOREIGN PATENT DOCUMENTS

| | | |
|---|---|---|
| EP | 3545862 A2 | 10/2019 |
| WO | WO 2018/234883 A1 | 12/2018 |
| WO | WO 2019/043507 A1 | 3/2019 |
| WO | WO 2019/130087 A1 | 7/2019 |

OTHER PUBLICATIONS

International Search Report and Written Opinion dated Nov. 9, 2020, for International Application No. PCT/IB2020/057972, 19 pages.
U.S. Appl. No. 62/868,457, entitled "Surgical Systems with Multiple RFID Tags," filed Jun. 28, 2019.

* cited by examiner

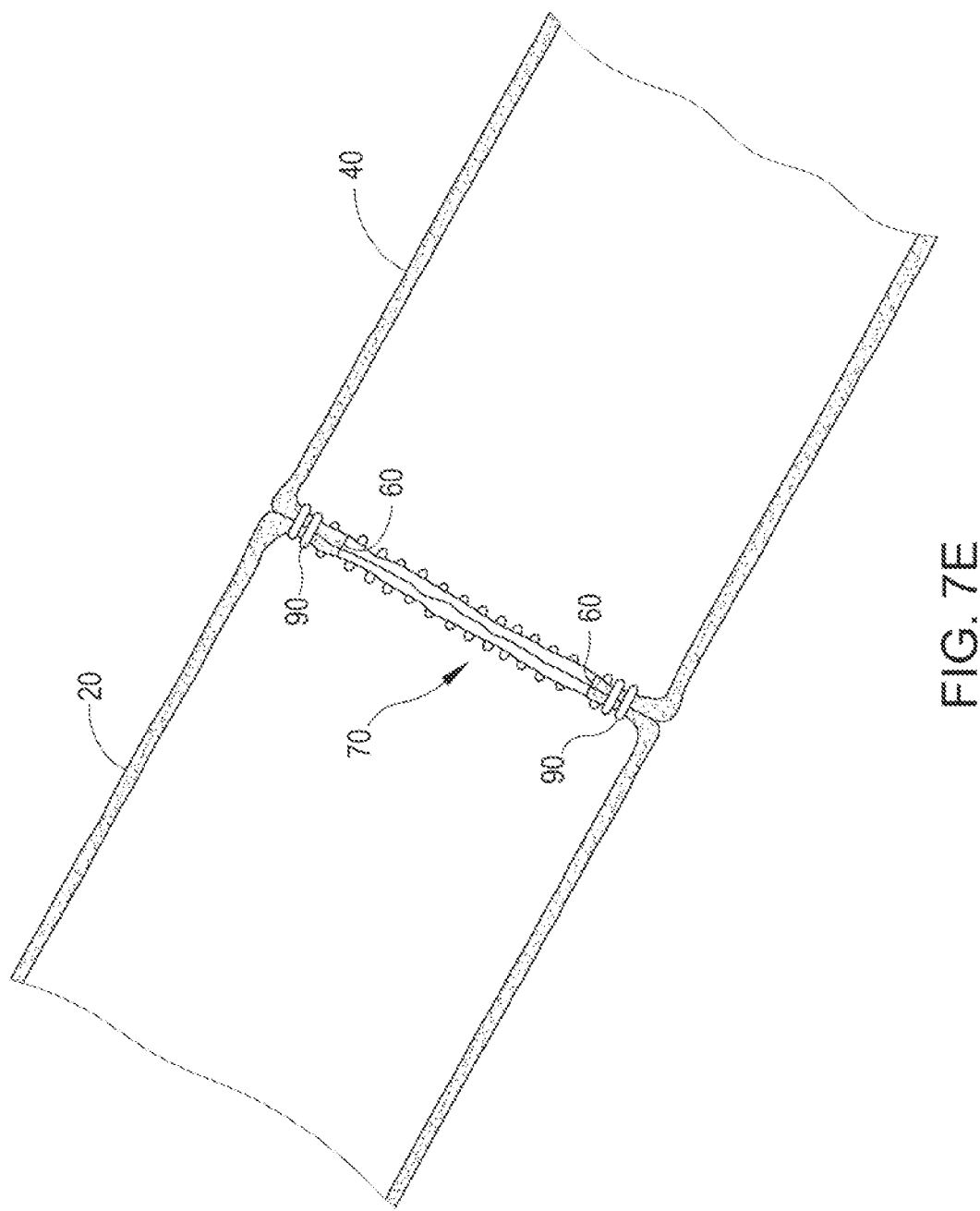

METHOD FOR CONTROLLING END EFFECTOR CLOSURE FOR POWERED SURGICAL STAPLER

This application is a continuation of U.S. Pat. App. No. 16/574,281, filed Sep. 18, 2019 and published as U.S. Pub. No. 2021/0077110 on Mar. 18, 2021, issued as U.S. Pat. No. 11,185,331 on Nov. 30, 2021.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7E depicts a cross-sectional side view of the first and second sections of the digestive tract of FIG. 7A joined together at an end-to-end anastomosis;

Figure 1:
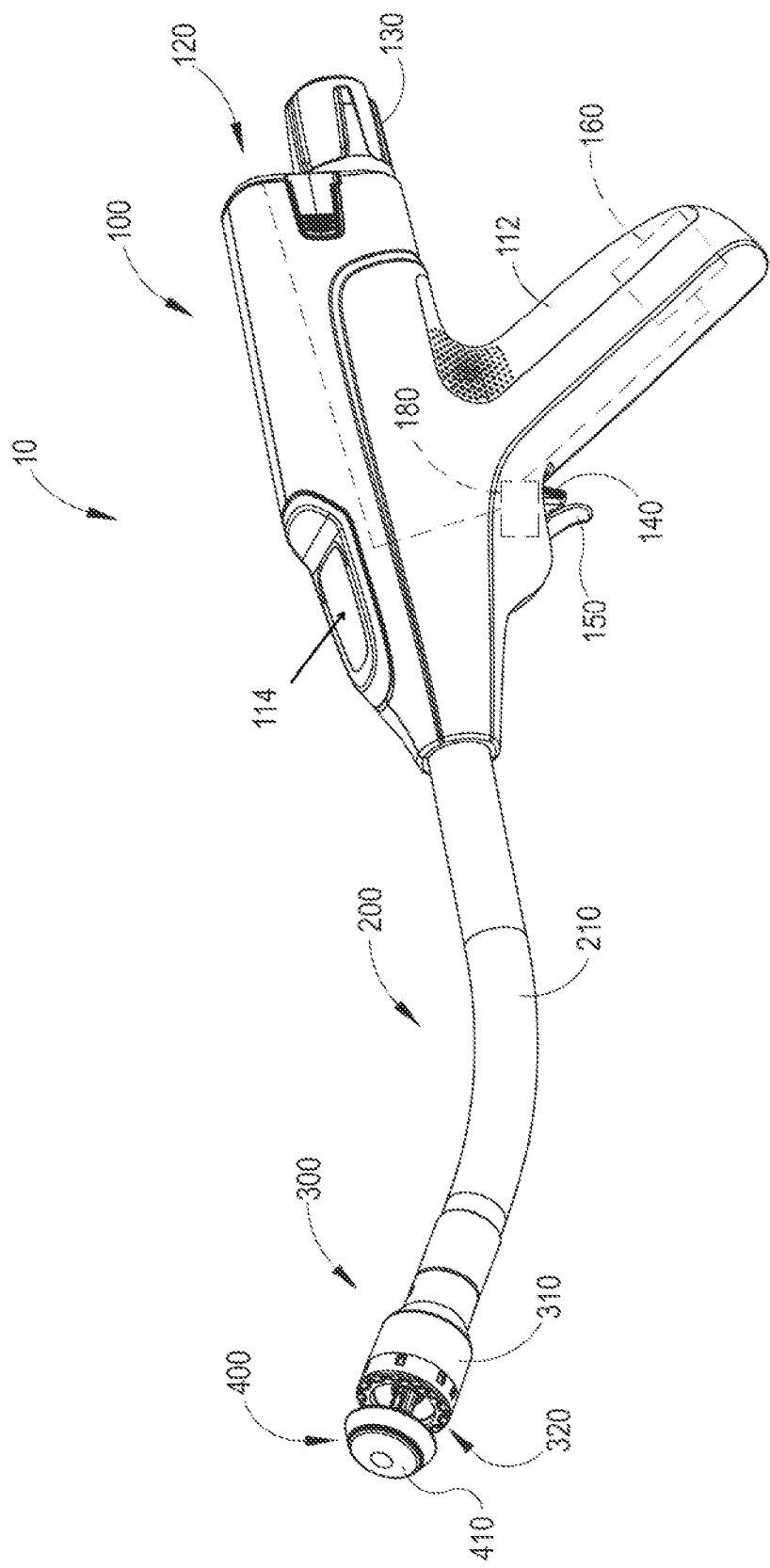
FIG. 1 depicts a perspective view of an exemplary circular surgical stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. OVERVIEW OF EXEMPLARY CIRCULAR SURGICAL STAPLING INSTRUMENT

Figure 2:
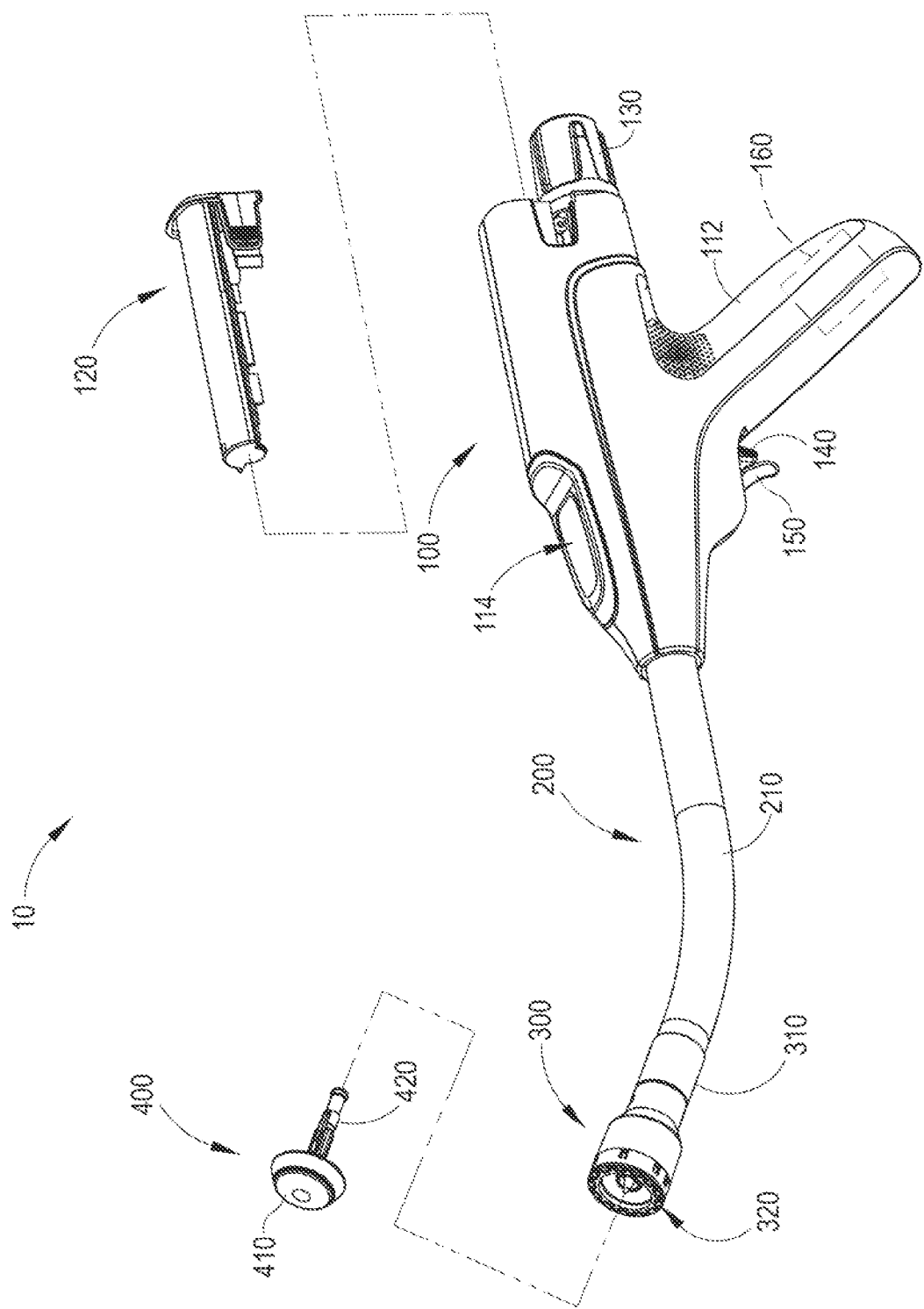
FIG. 2 depicts a perspective view of the circular stapler of FIG. 1, with a battery pack removed from a handle assembly and an anvil removed from a stapling head assembly.

FIGS. 1-2 depict an exemplary circular surgical stapling instrument (10) that may be used to provide an end-to-end, side-to-side, or end-to-end anastomosis between two sections of an anatomical lumen such as a portion of a patient's digestive tract. Instrument (10) of this example includes a body assembly (e.g. a handle assembly (100)), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

Figure 3:
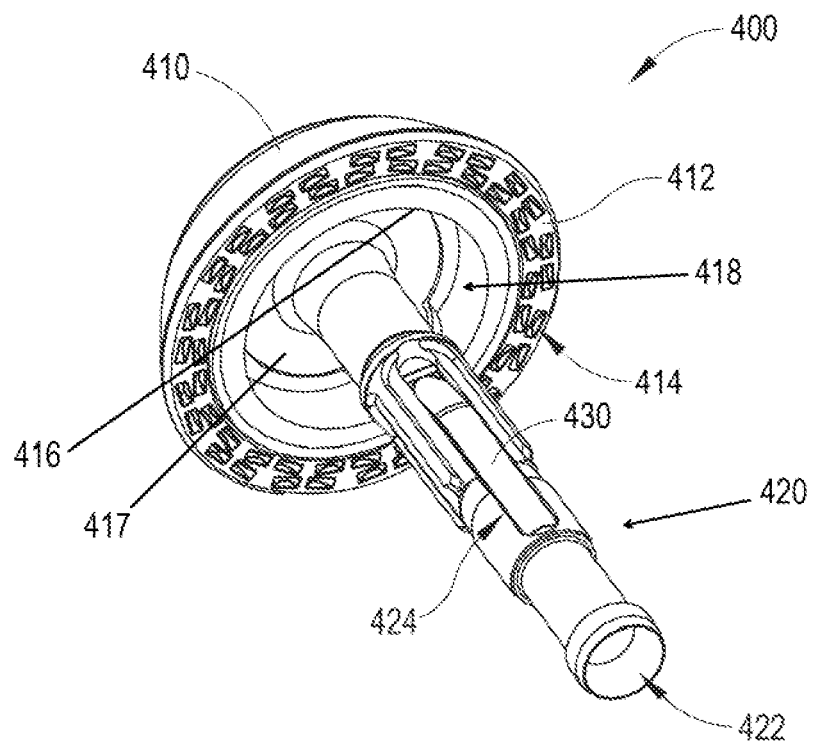
FIG. 3 depicts a perspective view of the anvil of the circular stapler of FIG. 1.

As best seen in FIG. 3, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. Proximal surface (412) terminates at an inner edge (416), which defines an outer boundary of an annular recess (418) surrounding shank (420).

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to pivot radially inwardly toward the longitudinal axis defined by shank (420). Latch members (430) thus act as retaining clips. This allows anvil (400) to be removably secured to an actuatable closure member in the form of a trocar (330) of stapling head assembly (300), as will be described in greater detail below. It should be understood, however, that latch members (436) are merely optional. Anvil (400) may be removably secured to trocar (330) using any other suitable components, features, or techniques.

B. Exemplary Stapling Head Assembly

Figure 4:
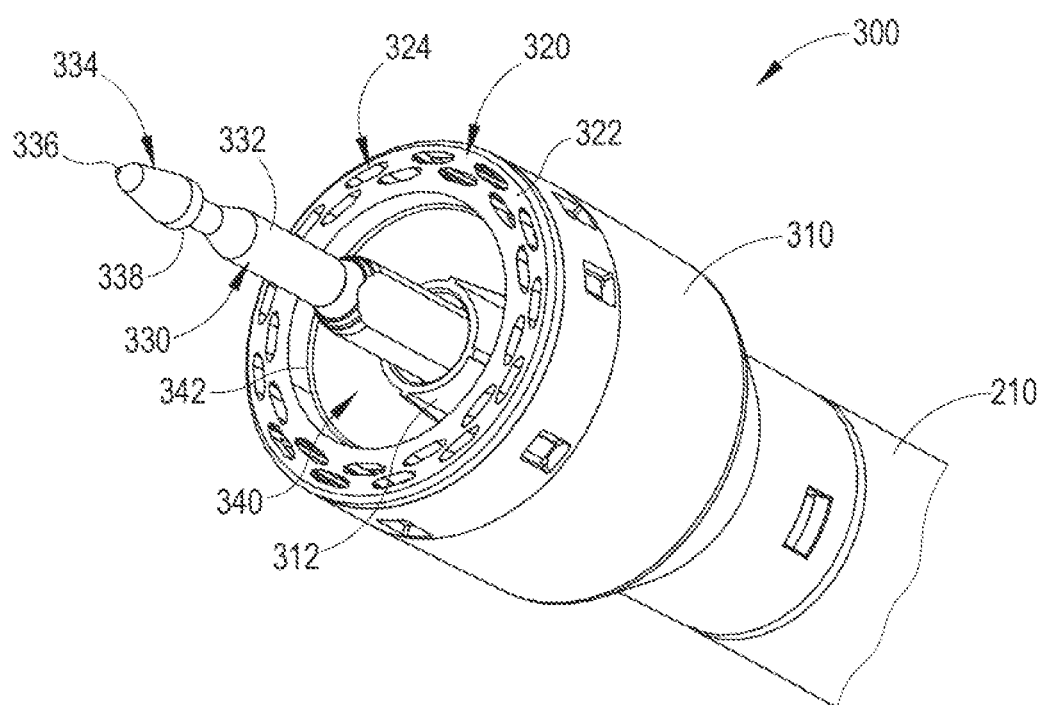
FIG. 4 depicts a perspective view of the stapling head assembly of the circular stapler of FIG. 1.
Figure 5:
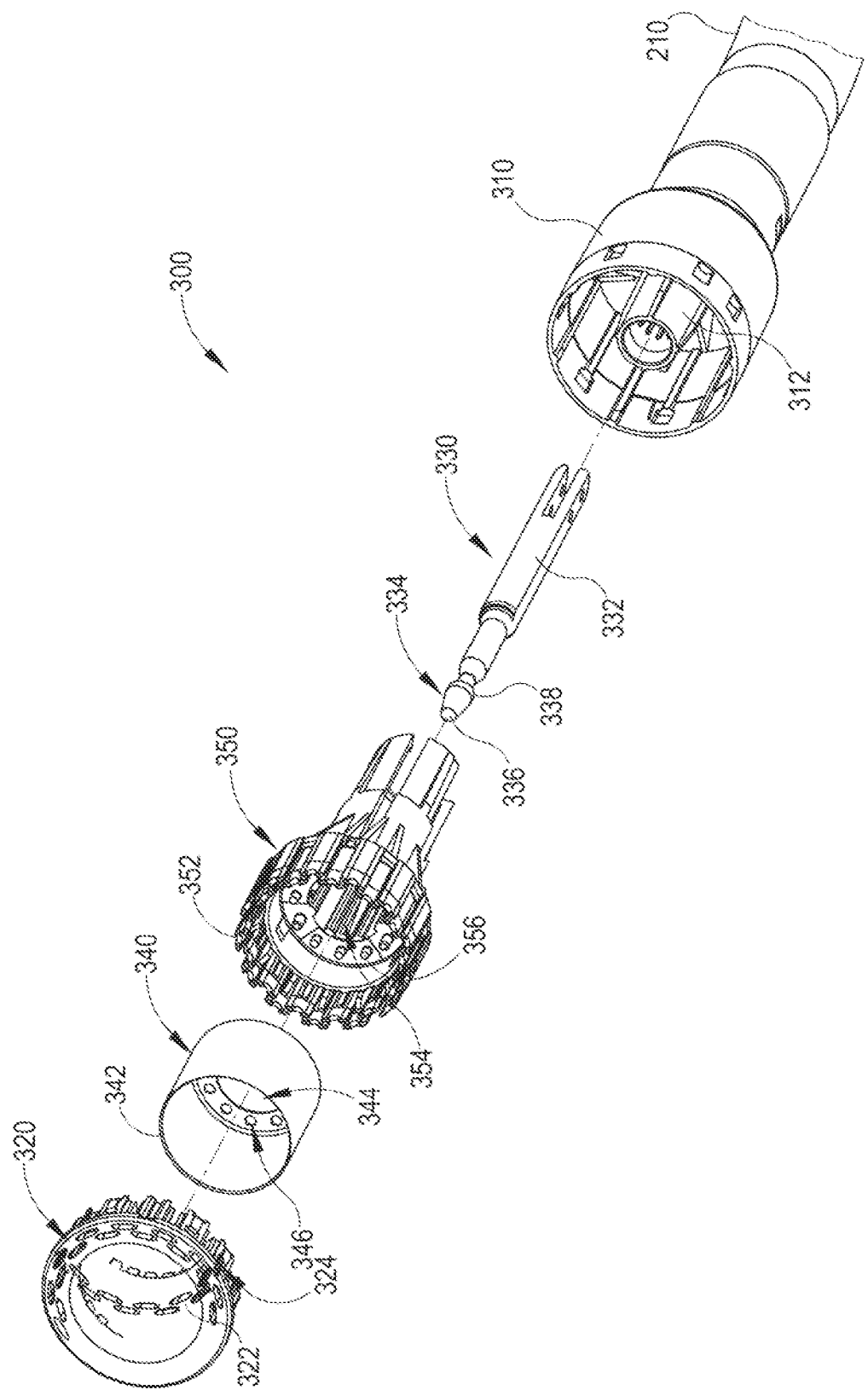
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a body member (310) and a staple driver member (350) slidably housed therein. Body member (310) includes a distally extending cylindraceous inner core member (312). Body member (310) is fixedly secured to an outer sheath (210) of shaft assembly (200), and body member (310) and outer sheath (210) thus serve together as a mechanical ground for stapling head assembly (300). In some versions, stapling head assembly (300) may be configured to releasably couple with the distal end of shaft assembly (200), for example as disclosed in U.S. Pat. No. 9,597,081, entitled "Motor Driven Rotary Input Circular Stapler with Modular End Effector," issued Mar. 21, 2017, the disclosure of which is incorporated by reference herein.

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. Staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple into a corresponding staple forming pocket (414) when stapling head assembly (300) is actuated. It should be understood that the arrangements of staple drivers (352) and staple forming pockets (414) shown herein may be modified in any suitable manner, provided that staple drivers (352) and staple forming pockets (414) are configured to align with one another to provide proper formation of staples. Staple driver member (350) also defines a bore (354) that is configured to coaxially receive core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and stapler driver member (350) will be apparent to those of ordinary skill in the art in view of the teachings herein.

A deck member (320) is fixedly secured to a distal end of body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified to correspond with the arrangement of drivers (352) and staple forming pockets (414) described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

Figure 9:
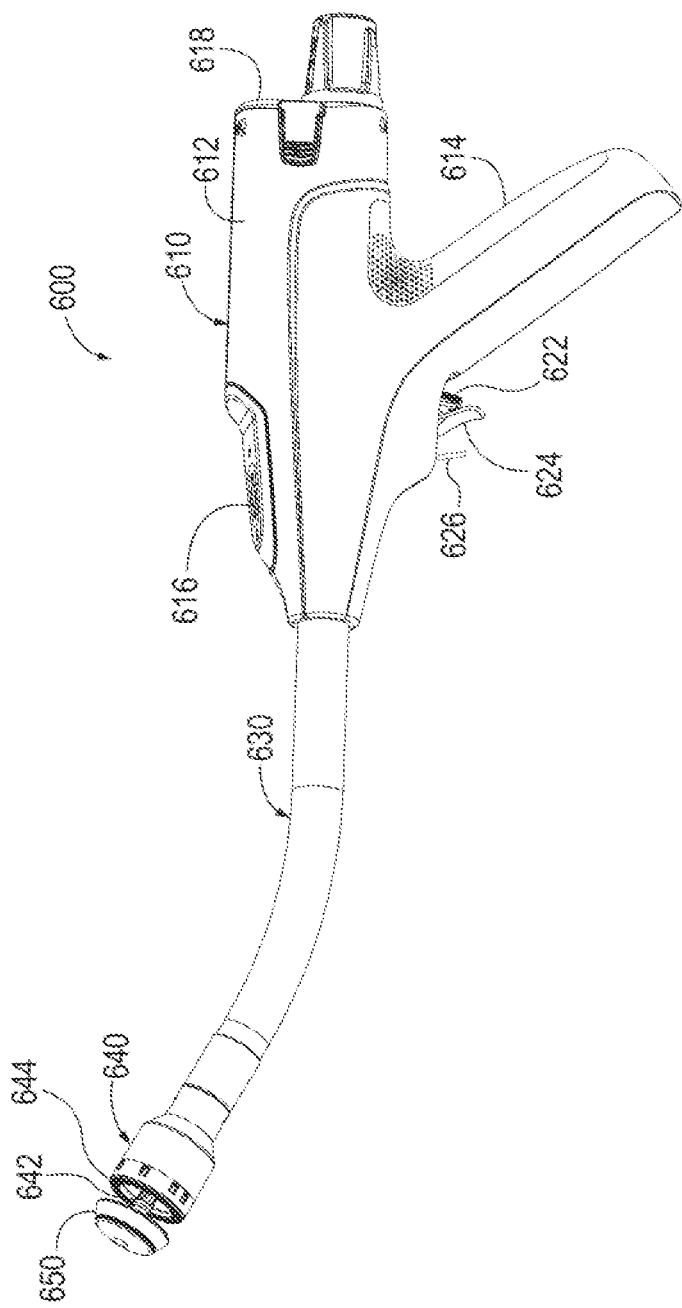
FIG. 9 depicts a perspective view of another exemplary circular surgical stapler.

As best seen in FIG. 9, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In some versions of instrument (10) it may be desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition, or in the alternative, features may be configured to prevent firing of stapling head assembly (300) unless anvil (400) is properly attached to trocar (330). For instance, if anvil (400) is not properly attached to trocar (330), stapling head assembly (300) may be prevented from firing. If anvil (400) is properly attached to trocar (330), firing of stapling head assembly (300) may be enabled. Such features may include various types of visual indicia, sensors, switches, and the like. By way of example only, such features may include those of the type disclosed in U.S. Pat. No. 10,307,157, entitled "Surgical Stapler with Anvil Seating Detection," issued Jun. 4, 2019, and U.S. Pub. No. 2017/0258471, entitled "Methods and Systems for Performing Circular Stapling," published Sep. 14, 2017, issued as U.S. Pat. No. 10,709,452 on Jul. 14, 2020, the disclosures of which are incorporated by reference herein.

C. Exemplary Shaft Assembly

Figure 6:
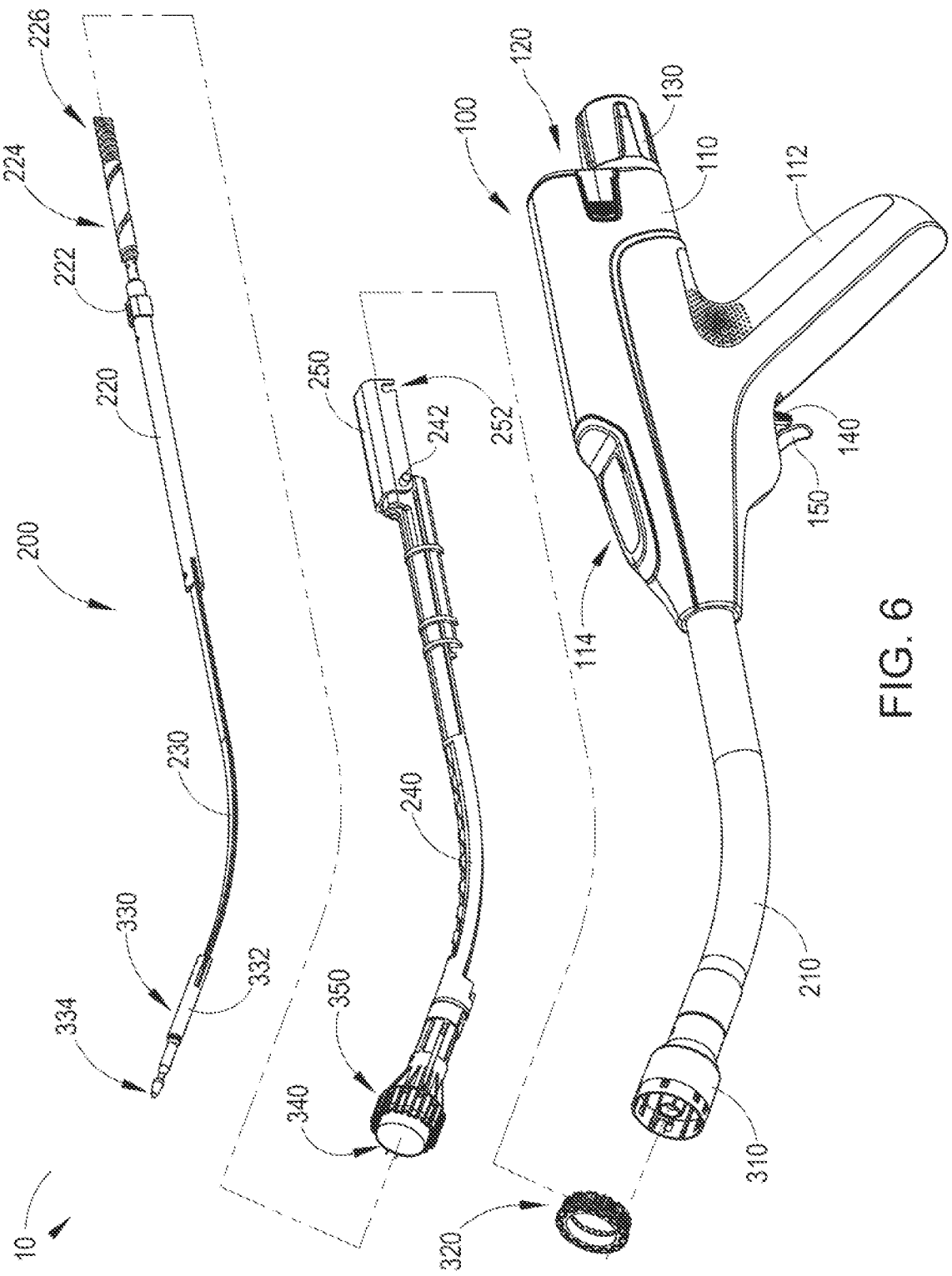
FIG. 6 depicts an exploded perspective view of the circular stapler of FIG. 1, with portions of the shaft assembly shown separated from each other.

FIG. 6 shows various components of shaft assembly (200), which couples components of stapling head assembly (300) with components of handle assembly (100). In particular, and as noted above, shaft assembly (200) includes an outer sheath (210) that extends between handle assembly (100) and body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140) a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust a gap distance (d) between opposing surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) of the present example includes an integral actuation paddle (not shown), which may be similar to the paddle disclosed in U.S. Pub. No. 2017/0258471, issued as U.S. Pat. No. 10,709,452, incorporated by reference above. The paddle is configured to actuate a switch of motor activation module (180) (FIG. 1) when firing trigger (150) is pivoted to a fired position. Motor activation module (180) is in communication with battery pack (120) and motor (160), such that motor activation module (180) is configured to provide activation of motor (160) with electrical power from battery pack (120) in response to the paddle actuating the switch of motor activation module (180). Thus, motor (160) will be activated when firing trigger (150) is pivoted. This activation of motor (160) will actuate stapling head assembly (300) via drive bracket (250), as described in greater detail below. Though not shown, and by way of example only, motor (160) may be operatively coupled with drive bracket (250) via a gearbox coupled with an output shaft of motor (160), a rotary cam member coupled with an output shaft of the gearbox, and a cam follower coupled with the rotary cam member, for example as disclosed in U.S. Pub. No. 2017/0258471, issued as U.S. Pat. No. 10,709,452, incorporated by reference above.

As best shown in FIGS. 1-2, handle assembly (100) is further configured to releasably receive a battery pack (120) operable to provide electrical power to motor (160), as noted above. It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is coupled with handle assembly (100). It should also be understood that, in some versions, battery pack (120) may be unitarily integrated within handle assembly (100) such that battery back (120) cannot be removed from handle assembly (100).

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. In some versions, one or more diseased portions of a patient's colon are removed, with the tubular anatomical structures (20, 40) of FIGS. 7A-7E representing the remaining severed portions of the colon.

Figure 7A:
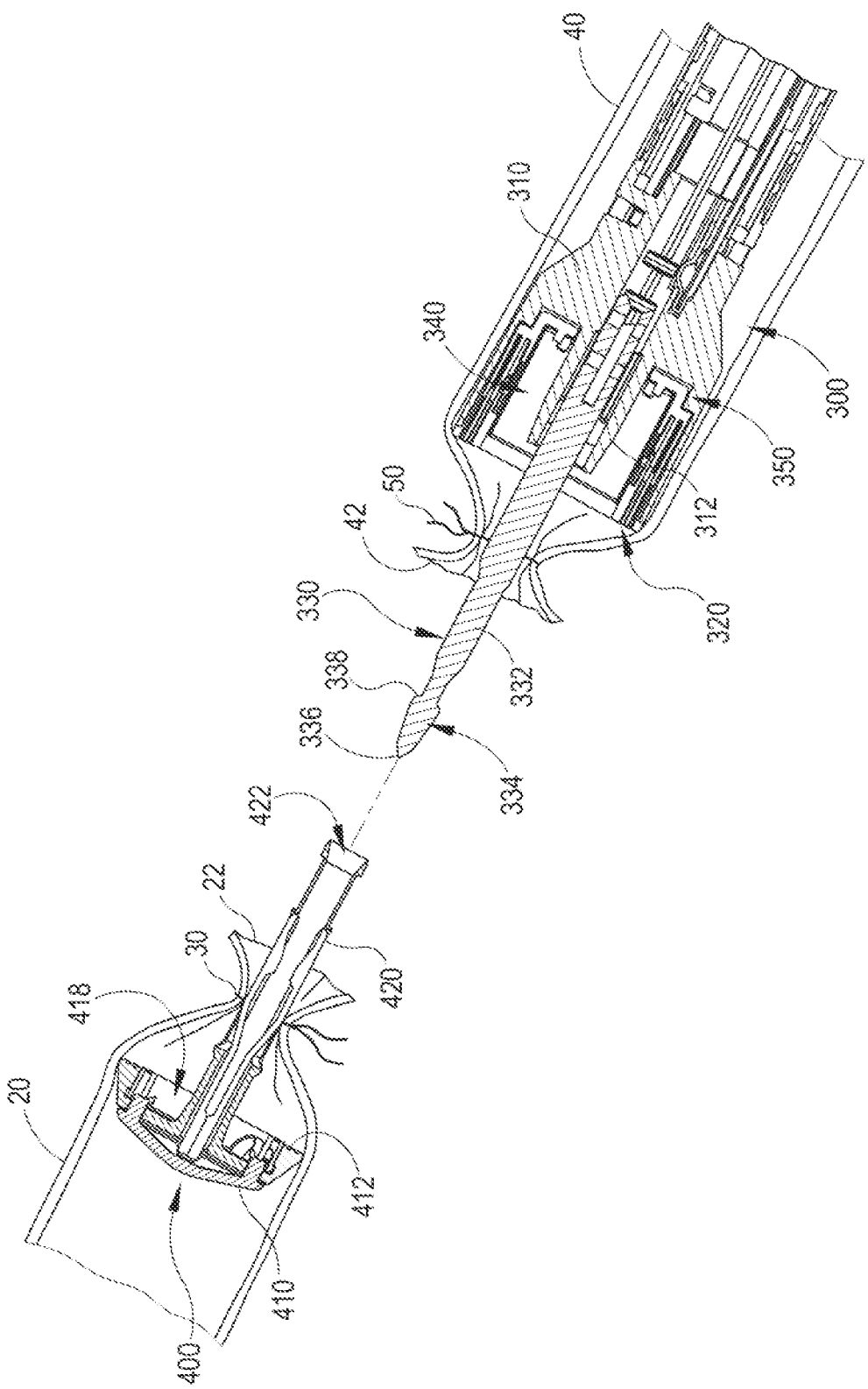
FIG. 7A depicts a cross-sectional side view of the anvil of FIG. 3 positioned within a first section of a digestive tract and the stapling head assembly of FIG. 4 positioned in a second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 7A-7E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
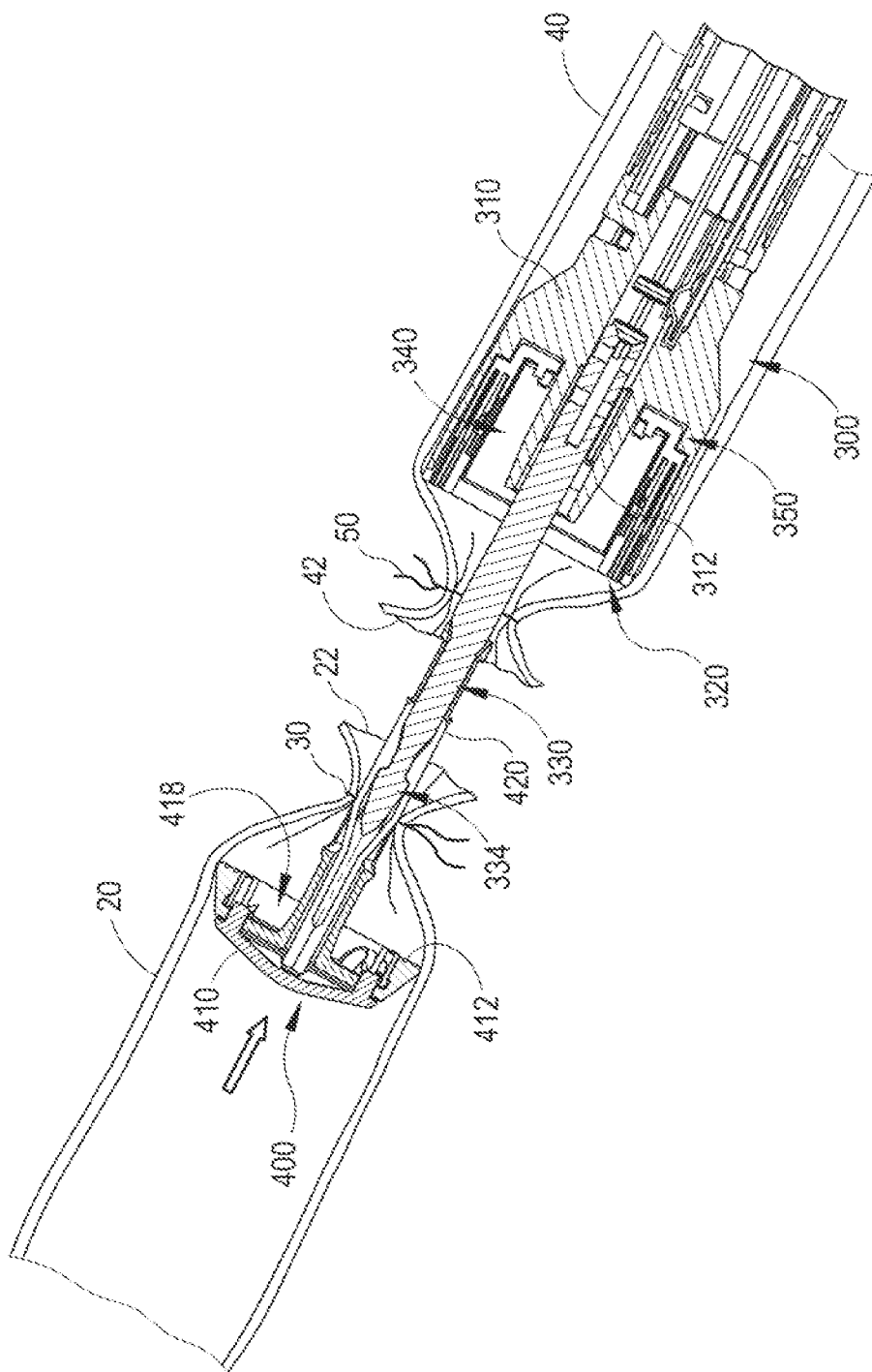
FIG. 7B depicts a cross-sectional side view of the anvil of FIG. 3 positioned within the first section of the digestive tract and the stapling head assembly of FIG. 4 positioned in the second section of the digestive tract, with the anvil secured to the stapling head assembly.
Figure 7C:
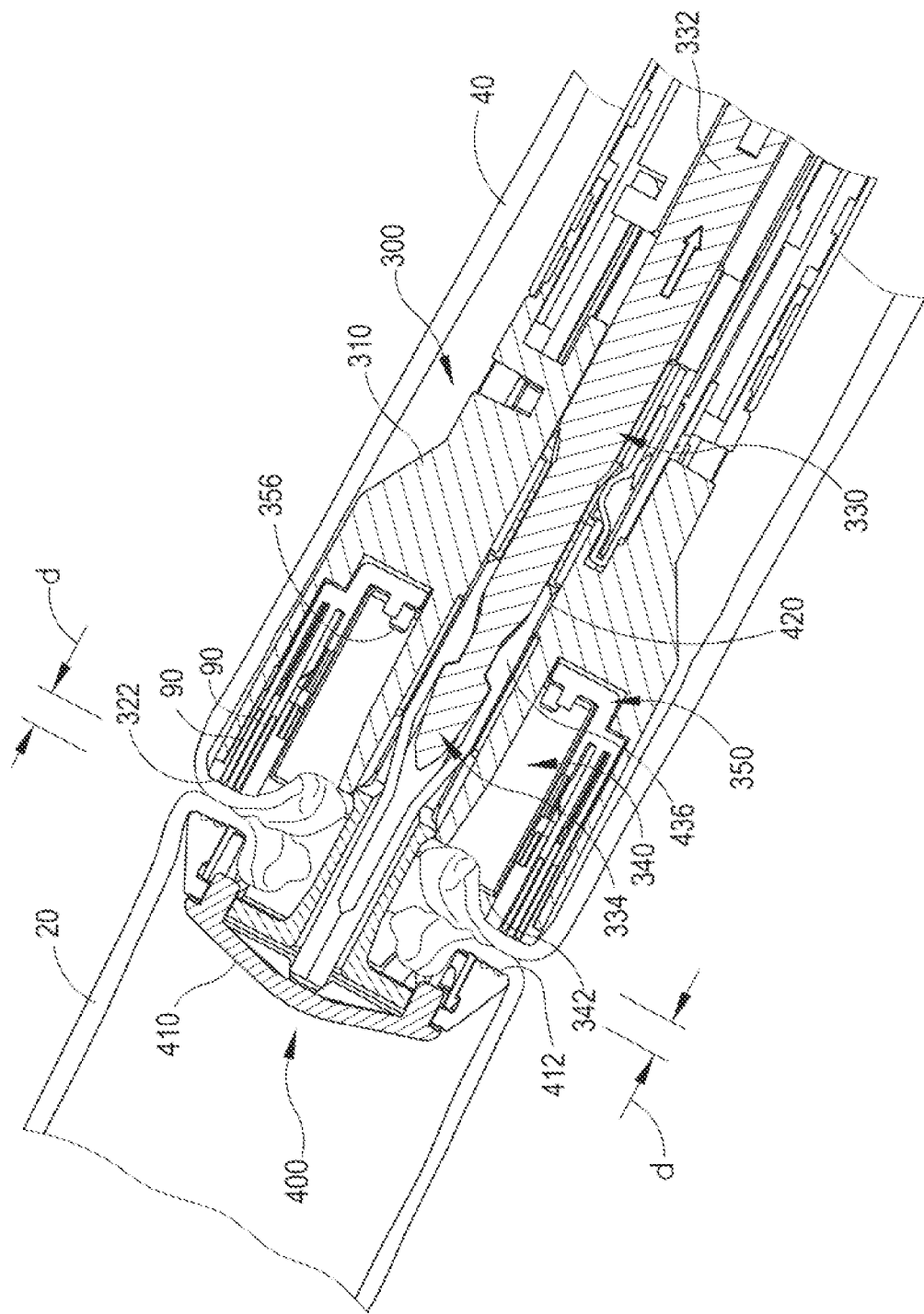
FIG. 7C depicts a cross-sectional side view of the anvil of FIG. 3 positioned within the first section of the digestive tract and the stapling head assembly of FIG. 4 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (522) within a user interface feature (114) of handle assembly (100) to determine whether the gap distance (d) between opposing surfaces (412, 322) of anvil (400) and stapling head assembly (300) is appropriate; and make any necessary adjustments via knob (130).

Figure 7D:
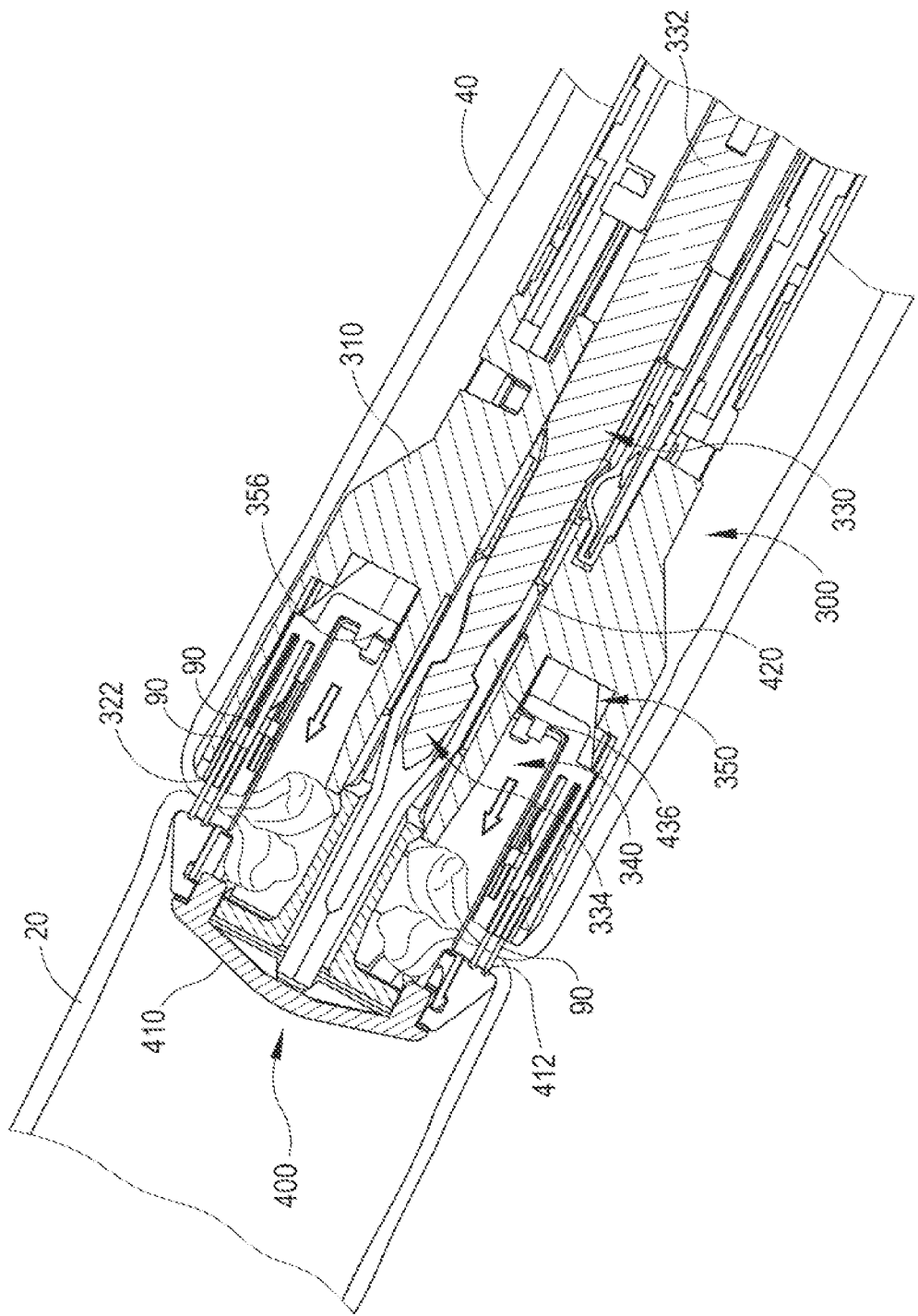
FIG. 7D depicts a cross-sectional side view of the anvil of FIG. 3 positioned within the first section of the digestive tract and the stapling head assembly of FIG. 4 positioned in the second section of the digestive tract, with the stapling head assembly actuated to sever and staple the clamped tissue.

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing paddle (158) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally, as shown in FIG. 7D. As knife member (340) translates distally, cutting edge (342) of knife member (340) cuts excess tissue that is positioned within annular recess (418) of anvil (400) and the interior of knife member (340).

As shown in FIG. 3, anvil (400) of the present example includes a breakable washer (417) positioned within annular recess (418). This washer (417) is broken by knife member (340) when the knife member (340) completes a full distal range of motion from the position shown in FIG. 7C to the position shown in FIG. 7D. Features of stapler (10) may be configured to provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

After the operator has actuated stapling head assembly (300) as shown in FIG. 7D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

F. Exemplary User Interface Feature of Handle Assembly

Figure 8:
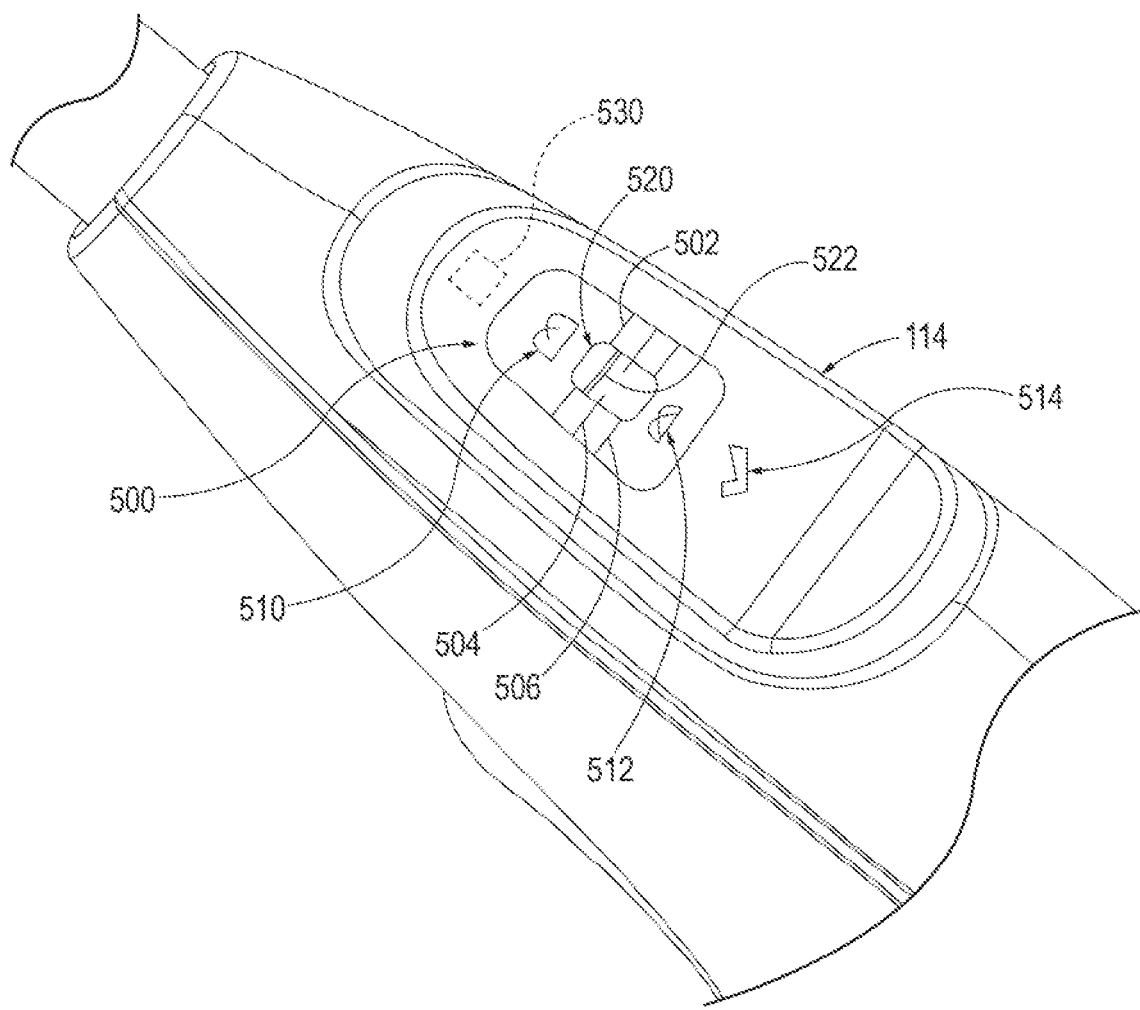
FIG. 8 depicts a perspective view of a user interface feature of the handle assembly of the circular stapler of FIG. 1.

As shown best in FIG. 8, handle assembly (100) of surgical stapling instrument (10) further includes a user interface feature (114) configured to provide the operator with visual feedback indicating the positioning of anvil (400) in relation to stapling head assembly (300) during a surgical procedure. The operator may thus observe user interface feature (114) while rotating knob (130) to confirm whether a suitable gap distance (d) between anvil (400) and stapling assembly (300) has been achieved.

User interface feature (114) of the present example includes a graphical indicator (500), which includes fixed linear indicia (502, 504, 506), graphical representations (510, 512) of staples, and a checkmark graphic (514). User interface feature (114) further defines a window (520) through which an indicator needle (522) may be viewed. In some variations, user interface feature (114) further includes a field (530) that may indicate a diameter associated with the size of stapling head assembly (300), the size of staples in stapling head assembly (300), the size of the gap defined between anvil (400) and stapling head assembly (300), and/or other information. By way of example only, field (530) may indicate a stapling head assembly (300) size of 23 mm, 25 mm, 29 mm, or 31 mm.

As the operator rotates knob (130) to adjust the longitudinal position of anvil (400) relative to stapling head assembly (300), the operator may observe the position of indicator needle (522) through window (520). Initially, indicator needle (522) may be positioned at or near the distal end of window (520). As anvil (400) continues to move proximally, indicator needle (522) will eventually move proximally relative to window (520). The operator may view the position of indicator needle (522) in relation to fixed linear indicia (502, 504, 506). The distal-most and proximal-most indicia (502, 506) may represent the boundaries of a "green zone," which is the acceptable range of distance between anvil (400) and stapling head assembly (300) for successful actuation of stapling head assembly (300). Thus, if indicator needle (522) is distal to distal-most indicia (502), the distance between anvil (400) and stapling head assembly (300) is too large; and if indicator needle (522) is proximal to proximal-most indicia (506), the distance between anvil (400) and stapling head assembly (300) is too small. Indicia (504) is longitudinally positioned between indicia (502, 506). Graphical representation (510) represents a relatively tall formed staple (e.g., suitable for use in relatively thick tissue); while graphical representation (512) represents a relatively short formed staple (e.g., suitable for use in relatively thin tissue). Graphical representations (510, 512) may thus facilitate the operator's decision, based on tissue observations or otherwise, on whether and how to achieve a desired formed staple height by selecting an appropriate corresponding spatial relationship between indicator needle (522) and indicia (502, 504, 506).

In the present example, window (520) is illuminated via a light emitting diode (LED) (not shown), further facilitating viewing of indicator needle (522) in window (520). In addition, checkmark graphic (514) is illuminated via another LED (not shown) when stapling head assembly (300) completes a stapling and cutting cycle. Thus, the operator may further rely on illumination of checkmark graphic (514) to confirm that the stapling and cutting cycle is complete, to thereby verify that it is safe to advance anvil (400) distally away from the anastomosis (70) to release the tissue and thereafter remove instrument (10) from the patient.

Circular surgical stapling instrument (10) may be further configured and operable in accordance with at least some of the teachings of U.S. Pub. No. 2017/0258471, issued as U.S. Pat. No. 10,709,452, incorporated by reference above.

II. EXEMPLARY CIRCULAR SURGICAL STAPLING INSTRUMENT HAVING INDEPENDENTLY CONTROLLED CLOSURE, STAPLING, AND CUTTING

In some instances, it may be desirable to provide a version of circular surgical stapling instrument (10) that exhibits powered actuation of anvil (400) in addition to powered actuation of internal firing components of stapling head assembly (300). Furthermore, it may be desirable to provide such a version of instrument (10) with a plurality of actuators that enable independent, powered actuation of anvil (400), staple driver member (350), and knife member (340), such that the resulting closure, stapling, and cutting strokes performed by such an instrument may be controlled independently from one another in response to user input.

While the teachings below are disclosed in the context of circular surgical staplers, it will be appreciated that such teachings may be applied to other types of surgical staplers as well. By way of example only, such other staplers may include right-angle surgical staplers of the type disclosed in U.S. Pat. No. 10,045,780, entitled "Method of Applying Staples in Lower Anterior Bowel Resection," issued Aug. 14, 2018, the disclosure of which is incorporated by reference herein.

A. Overview of Circular Surgical Stapling Instrument Having Independently Controlled Actuators FIG. 9 shows an exemplary circular surgical stapling instrument (600) that exhibits a configuration and functionality of the kind described above. It will be understood that instrument (600) is similar to instrument (10) described above except as otherwise described below. Similar to instrument (10), instrument (600) generally includes a body assembly in the form of a handle assembly (610), a shaft assembly (630) extending distally from handle assembly (610), a stapling head assembly (640) disposed at a distal end of shaft assembly (630), and an anvil (650) configured to releasably couple with an actuatable closure member in the form of a trocar (642). Anvil (650) is selectively retractable and extendable by trocar (642) relative to stapling head assembly (640) for clamping tissue against a distally facing deck surface (644) thereof. Stapling head assembly (640) is selectively operable to eject staples distally into the clamped tissue and against anvil (650), and to cut the clamped tissue with a cylindraceous knife member (not shown) similar to knife member (340) described above. Accordingly, stapling head assembly (640) and anvil (650) cooperate to define an end effector stapling assembly operable to clamp, staple, and cut tissue in response to user inputs.

Handle assembly (610) includes a casing (612) defining a pistol grip (614), a user interface (616) disposed on an upper side of casing (612) adjacent to a distal end of casing (612), and a knob (618) rotatably disposed at a proximal end of casing (612). User interface (616) and knob (618) are similar to user interface (114) and knob (130) described above except as otherwise described below. Casing (612) of the present example includes an open-ended proximal cavity (not shown) configured to releasably receive and retain a battery pack (620) similar to battery pack (120) and operable to power a motor unit (660) (see FIG. 10) housed within casing (612).

Handle assembly (610) of the present example further includes a safety member (622), a closure trigger (624), and a firing trigger (626) each movable independently relative to pistol grip (614). Actuation of closure trigger (624) is configured to activate motor unit (660) to initiate actuation of a trocar actuator (662) (see FIG. 10) and thereby effect closure of anvil (650) relative to stapling head assembly (640) to clamp tissue therebetween. Actuation of firing trigger (626) is configured to activate motor unit (660) to initiate actuation of a staple actuator (664) and a knife actuator (666) (see FIG. 10) to thereby staple and cut the clamped tissue. As described in greater detail below in connection with FIG. 11, instrument (600) is configured to control actuation of staple actuator (664) and knife actuator (666) independently in response to a single actuation of firing trigger (626). In this manner, a precise timing of the cutting stroke initiation relative to the stapling stroke initiation may be achieved.

Safety member (622) of the present example is in the form of a projection, such as a pivotable trigger similar to safety trigger (140), and is configured to directly or indirectly engage closure trigger (624) and/or firing trigger (626) to selectively block actuation thereof. For instance, safety member (622) may be configured to block actuation of closure trigger (624) until instrument (600) detects that anvil (650) has been fully attached to trocar (642). Additionally, or in the alternative, safety member (622) may be configured to block actuation of firing trigger (626) until anvil (650) has assumed a predetermined longitudinal position relative to stapling head assembly (640) that defines a particular gap distance (d) therebetween (see FIG. 7C).

Figure 10:
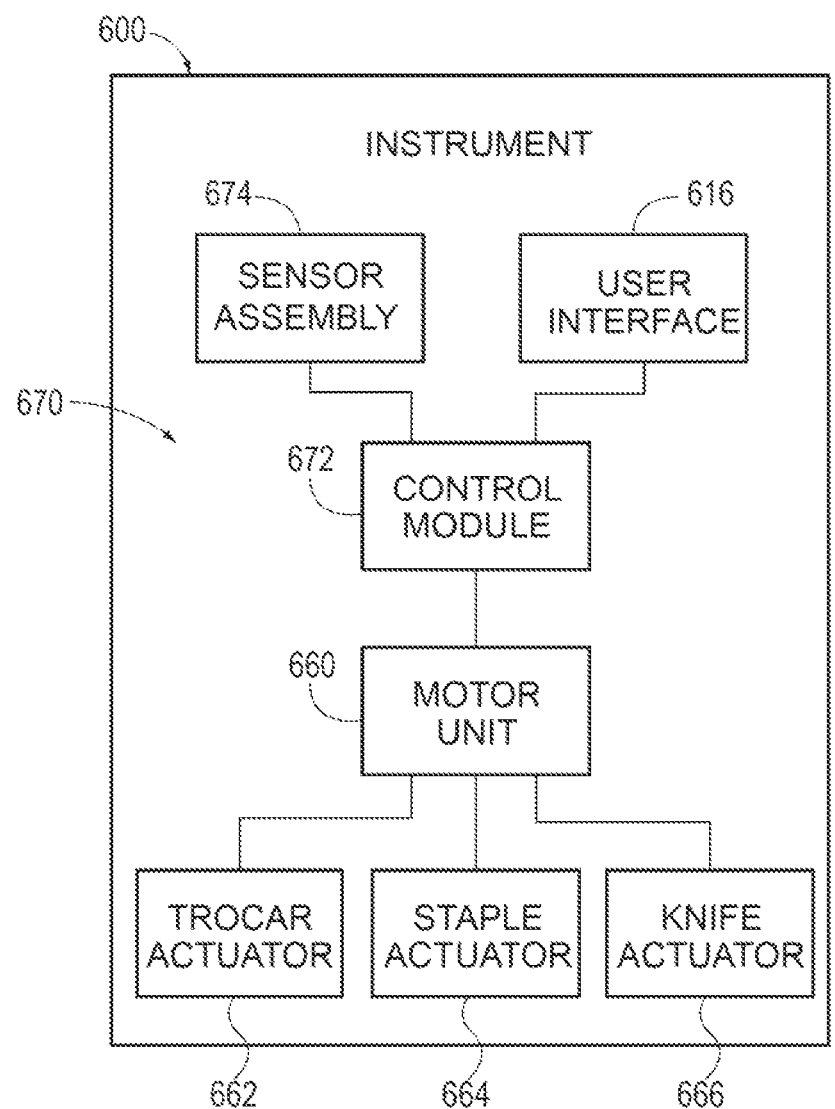
FIG. 10 depicts a schematic view of the circular stapler of FIG. 9, including a control system of the circular surgical stapler.

Actuators (662, 664, 666) of instrument (600), shown schematically in FIG. 10, are configured to operatively couple corresponding actuatable components of instrument (600) with motor unit (660). In particular, trocar actuator (662) operatively couples a trocar (642) with motor unit (660). Accordingly, trocar actuator (662) is configured to actuate trocar (642) and thus anvil (650) proximally and distally in response to activation of motor unit (660) when motor unit (660) is operatively engaged with trocar actuator (662). Trocar actuator (662) may include an elongate member similar to trocar actuation rod (220) combined with trocar actuation band assembly (230) of instrument (10), which is translatably disposed within shaft assembly (630).

Staple actuator (664) operatively couples a staple driver member (not shown) of stapling head assembly (640) with motor unit (660) independently of trocar actuator (662). Accordingly, staple actuator (664) is configured to actuate the staple driver member, and thus staples (not shown) housed within stapling head assembly (640), distally in response to activation of motor unit (660) when motor unit (660) is operatively engaged with staple actuator (664). Staple actuator (664) may include an elongate member similar to stapling head assembly driver (240) of instrument (10), which is translatably disposed within shaft assembly (630) independently of trocar actuator (662).

Knife actuator (666) operatively couples a cylindraceous knife member (not shown) of stapling head assembly (640) with motor unit (660) independently of trocar actuator (662) and staple actuator (664). Accordingly, knife actuator (666) is configured to actuate the knife member longitudinally in response to activation of motor unit (660) when motor unit (660) is operatively engaged with knife actuator (666). Knife actuator (666) may include an elongate member similar to stapling head assembly driver (240) of instrument (10), which is translatably disposed within shaft assembly (630) independently of trocar actuator (662) and staple actuator (664). In this manner, actuators (662, 664, 666) are configured to cooperate with motor unit (660) to provide independently actuated clamping of tissue, stapling of the tissue, and cutting of the tissue.

Knob (618) of handle assembly (610) of the present example is operatively coupled with trocar actuator (662) such that knob (618) is operable as an anvil closure bailout feature. In that regard, trocar actuator (662) is driven primarily by motor unit (660) but is also translatable longitudinally in response to rotation of knob (618), for example when motor unit (660) is deactivated or otherwise disengaged from trocar actuator (662). Accordingly, knob (618) may be rotated following partial or full proximal retraction of anvil (650) toward stapling head assembly (640) to thereby extend anvil (650) distally away from stapling head assembly (640), for example to release tissue captured therebetween. In such versions, knob (618) may be coupled with trocar actuator (662) via features similar to those described above in connection with knob (130) of instrument (10), including threaded portions (224, 226) of trocar actuation rod (220), for example. It will be understood, however, that knob (618) may be omitted from instrument (600) in some versions such that trocar actuator (662) is driven solely by motor unit (660).

Instrument (600) may be further configured and operable in accordance with at least some of the teachings of U.S. Pat. No. 9,445,816, entitled "Circular Stapler with Selectable Motorized and Manual Control," issued Sep. 20, 2016; U.S. Pat. No. 9,532,783, entitled "Circular Stapler with Select Motorized and Manual Control, Including a Control Ring," issued Jan. 3, 2017; U.S. Pat. No. 9,597,081, entitled "Motor Driven Rotary Input Circular Stapler with Modular End Effector," issued Mar. 21, 2017; U.S. Pat. No. 9,463,022, entitled "Motor Driven Rotary Input Circular Stapler with Lockable Flexible Shaft," issued Oct. 11, 2016; U.S. Pub. No. 2018/0368836, entitled "Surgical Stapler with Independently Actuated Drivers to Provide Varying Staple Heights," published Dec. 27, 2018, issued as U.S. Pat. No. 10,828,029 on Nov. 10, 2020; and/or any of the other patent references identified herein, the disclosures of which are incorporated by reference herein.

B. Exemplary Control System of Circular Surgical Stapling Instrument

As shown schematically in FIG. 10, instrument (600) further includes a control system (670) operable to control actuation of trocar actuator (662), staple actuator (664), and knife actuator (666) of instrument (600). Control system (670) includes a control module (672), motor unit (660), user interface (616), and a sensor (674) suitably arranged such that control module (672) communicates with each of motor unit (660), user interface (616), and sensor (674). Control module (672) includes a processor and is operable to store pre-programmed instrument control algorithms and receive input from user interface (616) and sensor (674). Based on these stored control algorithms and received input, control module (672) is configured to control motor unit (660) with pulse-width modulation (PWM) to drive actuation of trocar actuator (662), staple actuator (664), and knife actuator (666) independently from one another for clamping, stapling, and cutting tissue.

Motor unit (660) includes one or more motors and is operatively coupled with trocar actuator (662), staple actuator (664), and knife actuator (666). In some versions, motor unit (660) may comprise a single motor operatively coupled with and configured to drive all three actuators (662, 664, 666). In such versions, motor unit (660) may be coupled with actuators (662, 664, 666) via one or more power transmission assemblies (not shown), such as a gear assembly, various suitable types of which will be apparent to those of ordinary skill in the art in view of the teachings herein and in the incorporated references. In other versions, motor unit (660) may comprise three motors, each being dedicated to drive a respective one of actuators (662, 664, 666). In further versions, motor unit (660) may comprise two motors, a first motor of which is configured to drive trocar actuator (662) and a second motor of which is configured to drive staple actuator (664) and knife actuator (666) with assistance of a power transmission assembly. It will be understood that motor unit (660) may comprise various other quantities and arrangements of motors in other versions.

Sensor (674) is arranged within or otherwise coupled to stapling head assembly (640), shaft assembly (630), or handle assembly (610), and is operable to monitor one or more conditions of instrument (600) during use. For instance, sensor (674) may be configured to monitor translation of any one or more of actuators (662, 664, 666) and/or their adjoining components, such as trocar (642). In some such versions, sensor (674) may be mounted directly to any one of actuators (662, 664, 666) or an adjoining component thereof. In other such versions, sensor (674) may be fixedly mounted within stapling head assembly (640), shaft assembly (630), or handle assembly (610), such that actuators (662, 664, 666) and their adjoining components move relative to sensor (674).

In some versions, sensor (674) may be configured to detect secure attachment of anvil (650) to trocar (642), for example as disclosed in U.S. Pat. No. 10,307,157, incorporated by reference above; or in U.S. Pat. App. No. 16/574,299, entitled "Anvil Retention and Release Features for Powered Circular Surgical Stapler," filed on Sep. 18, 2019, published as U.S. Pub. No. 2021/0077093 on Mar. 18, 2021, issued as U.S. Pat. No. 11,185,324 on Nov. 30, 2021, the disclosure of which is incorporated by reference herein. In other versions, sensor (674) may be configured to detect certain characteristics of the particular stapling head assembly (640) coupled with shaft assembly (630), such as a diameter of stapling head assembly (640) or a size of the staples (not shown) housed therein. In some such versions, sensor (674) may be configured to detect such characteristics of stapling head assembly (640) via radio-frequency identification (RFID) of electronic information stored within a tag element disposed on or within stapling head assembly (640), for example as disclosed in U.S. Provisional Pat. App. No. 62/868,457, entitled "Surgical Systems with Multiple RFID Tags," filed on Jun. 28, 2019, the disclosure of which is incorporated by reference herein.

Still in other versions, sensor (674) may be in direct communication with motor unit (660). For instance, sensor (674) may comprise a current sensor operable to monitor an electrical current drawn by motor unit (660), or an encoder operable to monitor a rotational output of motor unit (660). Moreover, while only one sensor (674) is illustrated in the diagram of FIG. 10, it will be understood that sensor (674) may comprise a plurality of sensors, where each individual sensor (674) is configured to monitor and communicate with control module (672) regarding a respective one or more conditions of instrument (600). Furthermore, it will be understood that sensor (674) may be in the form of a sensor assembly that includes various suitable types of sensors readily apparent to those of ordinary skill in the art in view of the teachings herein and not otherwise described herein.

User interface (616) is similar to user interface (114) described above, except that user interface (616) is further configured to receive and communicate user input to control module (672). In that regard, user interface (616) may include one or more buttons, dials, other actuatable elements, or displayed graphics that are selectable by a user to indicate certain information pertaining to a surgical procedure to be performed or to stapling head assembly (640). By way of example only, such information may include any of the following: a desired staple formation height; a corresponding gap between anvil (650) and stapling7 head assembly (640) to which anvil (650) should be actuated during closure; a type or nominal thickness of tissue being fired upon with instrument (600); and/or a diameter of stapling head assembly (640). Such information, in combination with information provided by sensor (674), may be used by control module (672) to adjust strokes and/or rates of actuation of actuators (662, 664, 666), and/or to adjust timing pauses between the powered actuations of actuators (662, 664, 666) to ensure optimal clamping, stapling, and cutting of tissue during a procedure, for example as described in greater detail below.

C. Exemplary Method for Controlling Circular Surgical Stapler

Figure 11:
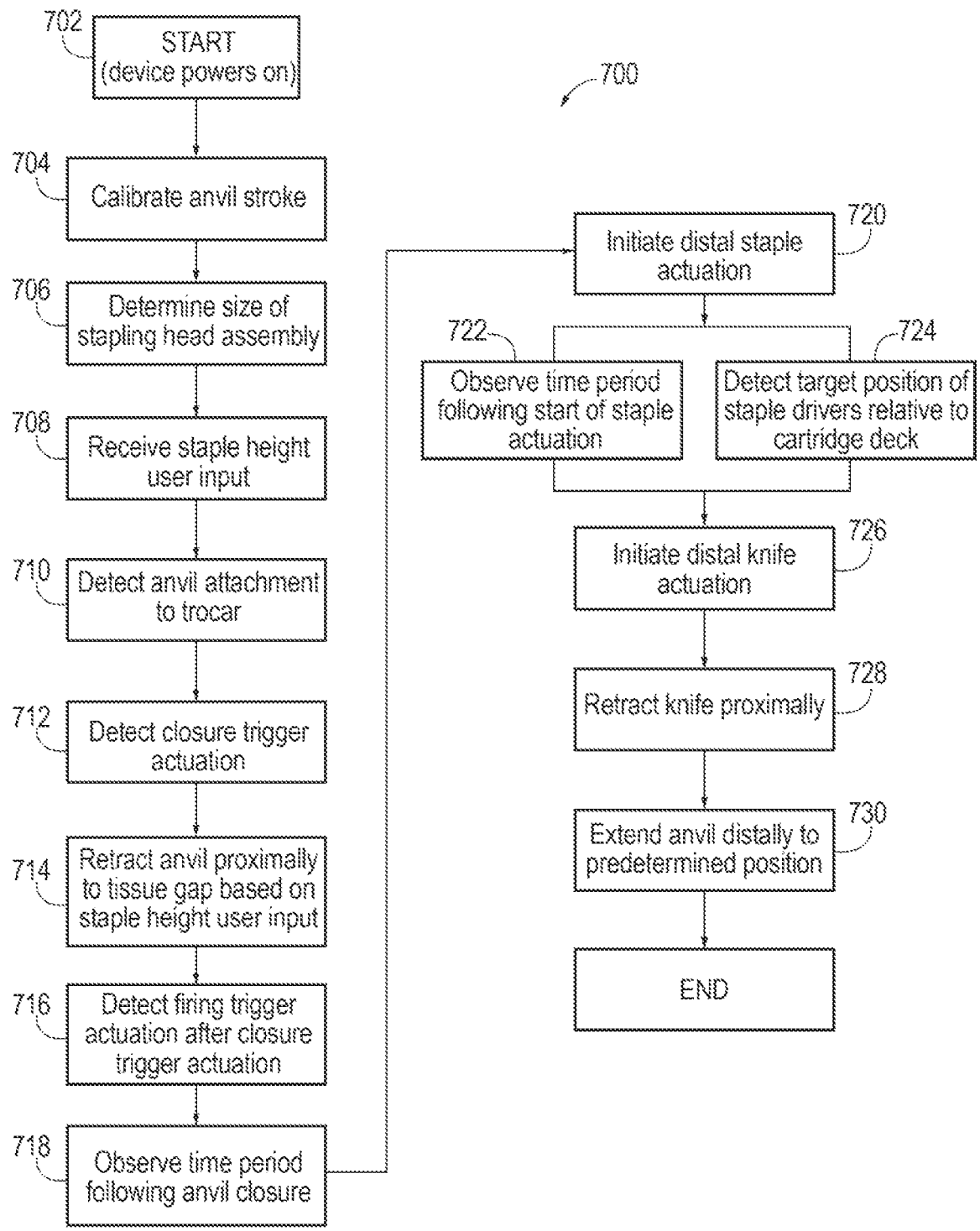
FIG. 11 depicts a diagrammatic view of an exemplary method for controlling the circular stapler of FIG. 9 via the control system of FIG. 10.

FIG. 11 shows an exemplary method (700) for controlling circular surgical stapling instrument (600) via control system (670) shown in FIG. 10. At step (702), instrument (600) powers on in response to being energized by battery pack (620), for example when battery pack (620) is fully inserted into the proximal end of handle assembly (610) after instrument (600) is removed from product packaging. Upon removal from the packaging, anvil (650) is already secured to trocar (642) and is in a fully open state, and a staple retainer (not shown) is secured to deck surface (644).

After instrument (600) powers on in the present example, control module (672) enters an anvil stroke calibration mode at step (704), which may occur automatically or in response to a user input, for example provided via user interface (616). In this calibration mode, control module (672) activates motor unit (660) to drive trocar actuator (662) to retract trocar (642) proximally and thereby close anvil (650) against the staple retainer, or alternatively against deck surface (644) in the event that the staple retainer has been removed. Control module (672) may detect that anvil (650) has reached a closed position by detecting via sensor (674) an increase in the electrical current load of motor unit (660) upon contact of anvil (650) with the staple retainer or deck surface (644). Control module (672) observes the stroke (i.e., longitudinal displacement) of anvil (650) during this retraction process and compares it to an expected stroke of anvil (650). Based on this comparison and any differences observed between the two stroke values, control module (672) then calibrates an actuation algorithm that is executed to activate motor unit (660) to actuate trocar actuator (662), and thereby ensure precise actuations of anvil (650) thereafter during a surgical procedure. In addition, or in the alternative, calibration of the anvil stroke may be performed by control module (672) in real time during a surgical procedure when anvil (650) is being retracted to clamp tissue. Such calibration of the anvil stroke is described in further detail below. It will be understood that the strokes of one or more other actuatable members of instrument (600) may be calibrated in a similar manner before or during a surgical procedure, and also that the calibration of the anvil closure stroke may be applied by control module (672) to also calibrate the stapling stroke and/or the cutting stroke of instrument (600).

At step (706), control module (672) determines a diameter of stapling head assembly (640). As described above, stapling head assembly (640) may be releasably attached to shaft assembly (630) such that stapling head assemblies (640) of various diameters may be interchangeably coupled with the distal end of shaft assembly (630) depending on a lumen size of the tissue structure being operated on with instrument (600). Control module (672) is configured to make this size determination based on user input provided via user interface (616) and/or information provided by sensor (674), for instance when sensor (674) is configured to detect the size of stapling head assembly (640) in the manner described above.

At step (708), control module (672) receives from user interface (616) input that indicates a desired height of staples to be formed in tissue, as selected by the operator via user interface (616). Control module (672) equates this staple height to a corresponding gap distance (d) (see FIG. 7C) to be established between anvil (650) and deck surface (644) of stapling head assembly (640) at a closed position of anvil (650), in order to achieve the selected staple height.

While steps (704, 706, 708) are shown in FIG. 11 as being performed in a particular order, it will be appreciated that these steps (704, 706, 708) may be performed in a variety of orders relative to one another following the powering on of instrument (600) in step (702) and before the actuation of staple actuator (664) described below.

Following completion of steps (704, 706, 708), the operator detaches anvil (650) from trocar (642) and proceeds to position anvil (650) within a first tubular tissue structure of a patient and separately position stapling head assembly (640) within a second tubular tissue structure of the patient. The operator then attaches anvil (650) to trocar (642) within the patient, for example as shown in FIGS. 7A-7B described above, at which point control module (672) detects at step (710) that the attachment has been made. Such detection may be made by sensor (674), which communicates a corresponding signal to control module (672).

At step (712), control module (672) detects that closure trigger (624) has been actuated by the operator. Control module (672) then proceeds to step (714) and directs motor unit (660) to drive trocar actuator (662) to actuate trocar (642) proximally and thereby retract anvil (650) to a closed position at which the selected staple height and corresponding gap distance (d) are achieved. In some versions, control module (672) may be configured to initiate retraction of trocar (642) and anvil (650) only in response to an actuation of closure trigger (624) that occurs after attachment of anvil (650) to trocar (642) has been detected at step (710). The operator may monitor the retraction of anvil (650) toward its closed position via visual indicia and/or displayed graphics of user interface (616).

Additionally, in some versions, control module (672) may control motor unit (660) to retract anvil (650) proximally through the anvil closure stroke in two sequential stages. For instance, control module (672) may direct motor unit (660) to retract anvil (650) through a first portion of the anvil closure stroke, at which point control module (672) pauses activation of motor unit (660) for a predetermined period of time (e.g., several seconds). At the end of this wait period, control module (672) reactivates motor unit (660) to continue retracting anvil (650) through the remaining portion of the anvil closure stroke to its closed position. Inclusion of such a pause in the retraction of anvil (650) may enable the tissue being compressed between anvil (650) and deck surface (644) to at least partially settle (or "creep"). Advantageously, this settling of tissue yields a reduction of the axial extension load on trocar (642) and the resulting electrical current load of motor unit (660) as anvil (650) advances proximally to its fully closed position defined by the target staple height input provided by the user in step (708).

At step (716), control module (672) detects that firing trigger (626) has been actuated by the operator following completion of the anvil closure stroke. In the present example, in response to detecting this actuation, control module (672) observes completion of a predetermined period of time measured from completion of the anvil closure stroke, during which staple actuator (664) and knife actuator (666) remain stationary. This wait period after anvil closure enables the clamped tissue to settle (or "creep") into its fully compressed state before stapling head assembly (640) is fired, thus reducing the axial forces on staple actuator (664) and knife actuator (666), and the resulting current loads of motor unit (660), during the respective stapling and cutting sequences. It will be understood that this wait period may be omitted in some versions.

Upon completion of the wait period denoted in step (718), control module (672) initiates distal actuation of the staple driver member (not shown) at step (720) to begin stapling the clamped tissue. In particular, control module (672) activates motor unit (660) to engage and drive staple actuator (664) to actuate the staple driver member distally through stapling head assembly (640) and thereby drive staples into tissue and against anvil (650), for example similar to the manner shown in FIG. 7D. Upon initiating actuation of staple actuator (664), control module (672) at step (722) observes another predetermined period of time during which motor unit (660) continues to drive staple actuator (664) through the stapling stroke. Simultaneously, at step (724) control module (672) communicates with sensor (674) to detect when the staple driver member reaches a predetermined longitudinal position within stapling head assembly (640). Such a position may correspond to the point at which individual staple drivers (not shown), similar to staple drivers (352) described above, reach deck surface (644) such that the staples are at least partially formed within the clamped tissue. This process is described in further detail below in connection with FIGS. 17-19, and in U.S. Pat. App. No. 16/574,797, entitled "Method for Controlling Cutting Member Actuation for Powered Surgical Stapler," filed on Sep. 18, 2019, published as U.S. Pub. No. 2021/0077112 on Mar. 18, 2021, issued as U.S. Pat. No. 11,123,074 on Sep. 21, 2021, the disclosure of which is incorporated by reference herein.

In response to detecting completion of the predetermined time period of step (722) and/or detecting at step (724) that the staple driver member has reached the predetermined longitudinal position, control module (672) then initiates distal actuation of the knife member (not shown) at step (726) to begin cutting the tissue. In particular, control module (672) activates motor unit (660) to engage and drive knife actuator (666) to actuate the knife member distally through stapling head assembly (640) and thereby cut the tissue, for example similar to the manner shown in FIG. 7D.

As noted above, delaying initiation of the cutting stroke relative to initiation of the stapling stroke, as enabled by independent actuation of staple and knife actuators (662, 664, 666), ensures at least partial formation of staples within the tissue before tissue cutting commences. Advantageously, this approach enables the staples to anchor within the clamped tissue before cutting, and thereby prevent lateral shifting of the tissue and resulting malformation of the staples when the knife member is driven distally.

The end of the distal cutting stroke of the knife member may correspond to a point at which the knife member breaks a washer (not shown) within anvil (650) similar to washer (417) described above. Upon completion of the distal cutting stroke, control module (672) at step (728) directs motor unit (660) to retract the knife member proximally back into stapling head assembly (640). In some versions, knife member distal extension and subsequent proximal retraction may be achieved by powering motor unit (660) through a continuous, uniform range of motion, for example as disclosed in U.S. Pub. No. 2017/0258471, issued as U.S. Pat. No. 10,709,452, incorporated by reference above. In other versions, control module (672) may be programmed to communicate with sensor (674) to detect completion of the distal cutting stroke, and thereafter specifically direct motor unit (660) to drive knife actuator (666) in an alternative manner to retract the knife member proximally. In any of such versions, sensor (674) may comprise an encoder configured to monitor a rotational output of motor unit (660).

Simultaneously with or subsequently to knife retraction step (728), control module (672) at step (730) directs motor unit (660) to drive trocar actuator (662) distally to thereby extend anvil (650) distally to a predetermined position relative to deck surface (644) of stapling head assembly (640). This distal extension enables the stapled tissue to be released from between anvil (650) and stapling head assembly (640) so that instrument (600) may be withdrawn from the patient while anvil (650) remains attached to trocar (642).

III. EXEMPLARY METHOD FOR CALIBRATING CLOSURE RATE AND/OR CLOSURE STROKE

As described above, it may be desirable to refine the longitudinal actuation ("closure stroke") and/or rate of actuation ("closure rate") of longitudinal actuation of a movable member for improved clamping. Proper calibration of this closure stroke and/or closure rate enables circular stapler (600) to more precisely clamp patient tissue. As will be described in greater detail below, tissue compression may be improved by monitoring initial tissue contact, gap, and/or force to control the closure rate and/or the closure stroke.

Control module (672) of the present example is configured to store and execute a movable member actuation algorithm (e.g. including closure stroke and closure rate) to longitudinally actuate trocar actuator (662) (and thus trocar (642) and anvil (650)) to clamp tissue. It may be desirable to calibrate trocar actuator (662), staple actuator (664), and knife actuator (666) before or during a surgical procedure. Control module (672) of the present example is configured to store and execute a staple driver member actuation algorithm to longitudinally actuate staple actuator (664) (and thus staple driver member) to staple tissue. Control module (672) of the present example is configured to store and execute a knife member actuation algorithm to longitudinally actuate knife actuator (666) (and thus knife member) to cut tissue. Each of these actuation algorithms stored by control module (672) includes a correlation between a given rotational output of motor unit (660) and an expected longitudinal displacement of the corresponding actuated member of instrument (600) effected by that particular rotational output. As described above, the rotational output of motor unit (660) may be monitored by an encoder operatively coupled with motor unit (660) and in communication with control module (672). As described below, the longitudinal strokes of actuators (662, 664, 666) may be calibrated by adjusting the corresponding actuation algorithms stored by control module (672).

A. First Exemplary Method to Adjust Closure Rate and/or Closure Stroke

Figure 12:
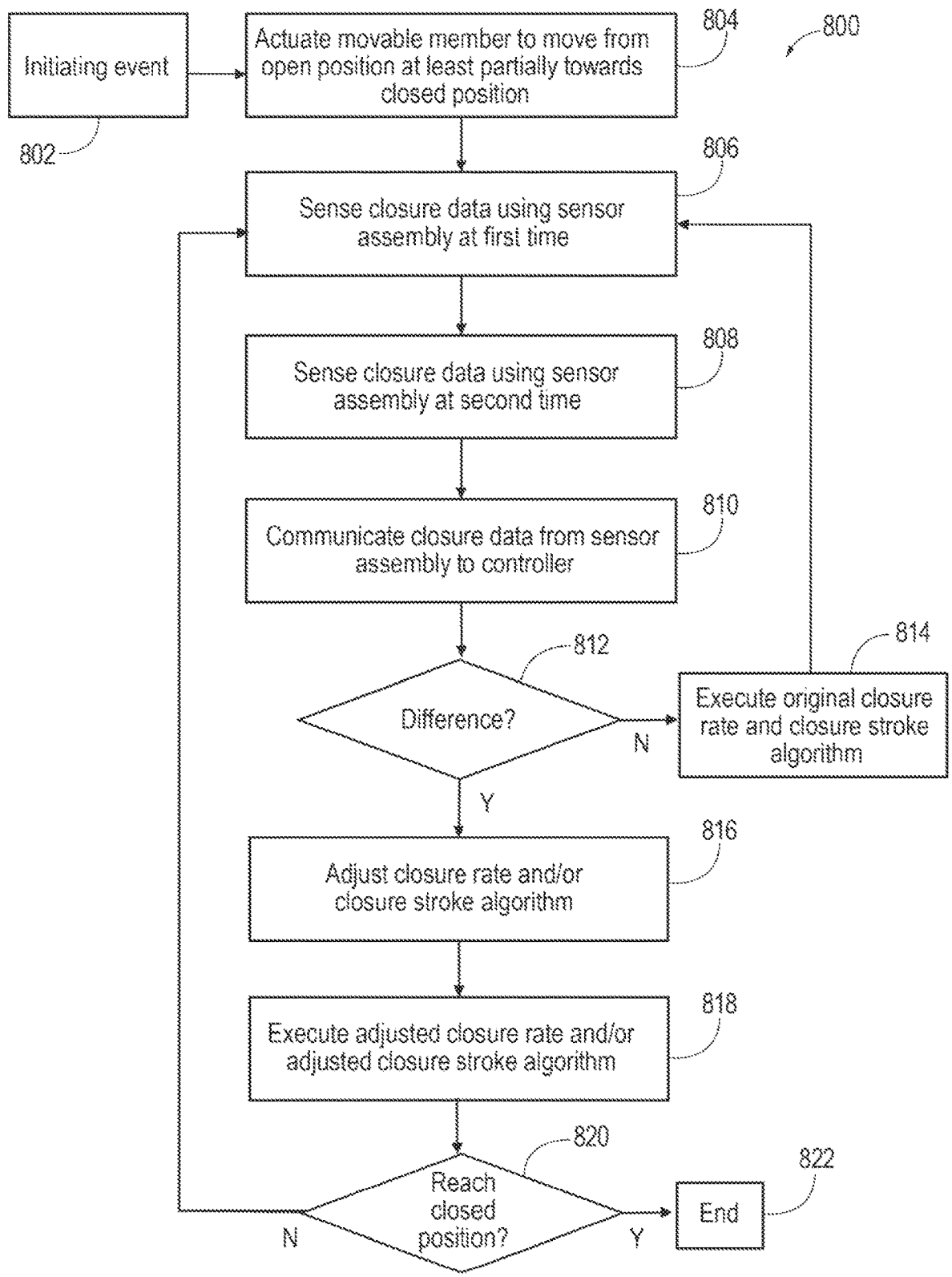
FIG. 12 depicts a diagrammatic view of an exemplary method for calibrating closure rate and closure stroke of a movable member of the circular stapler of FIG. 9 by adjusting actuation algorithms executed by the control system of FIG. 10.

An exemplary method (800) of operating a powered surgical stapler, such as circular surgical stapling instrument (600), is shown and described with reference to FIG. 12. Particularly, FIG. 12 shows a diagrammatic view of method (800) for calibrating the closure rate and/or closure stroke of the movable member (e.g. trocar (642), anvil (650), or trocar actuator (662)) of instrument (600) of FIG. 9 by adjusting actuation algorithms executed by control system (670) of FIG. 10. As previously described with reference to FIG. 9, instrument (600) includes motor unit (660), shaft assembly (630) operatively coupled with motor unit (660), a controller (e.g. control module (672)) in communication with motor unit (660), and sensor assembly (674) in communication with control module (672), anvil (650), and deck surface (644) that opposed anvil (650). The movable member (e.g. trocar (642), and anvil (650), or trocar actuator (662) shown in FIG. 13) is actuatable between an open position and a closed position. In the open position (similar to FIG. 7C with referencing instrument (10)), trocar (642) is configured to receive at least first and second tissue layers (T1, T2) between deck surface (644) and anvil (650). In the closed position (similar to FIG. 7D referencing instrument (10)), anvil (650) and deck surface (644) compress at least first and second tissue layers (T1, T2) together.

As shown in FIG. 12, method (800) begins at step (802) with an initiating event, which may be an actuation of closure trigger (624) following attachment of anvil (650) to trocar (650) during the surgical procedure. In response to the initiating event, control module (672) executes the stored movable member actuation algorithm at step (804) to activate motor unit (660) to actuate trocar actuator (662) proximally to transition anvil (650) from the open position towards the closed position. Prior to or during execution of the movable member actuation algorithm, control module (672) determines that a monitored one of trocar (642), anvil (650), or trocar actuator (662) is in a predetermined position, e.g. via detection by sensor assembly (674) using position sensor (680). By way of example only, the predetermined position may correspond to anvil (650) in a fully open position.

Figure 13:
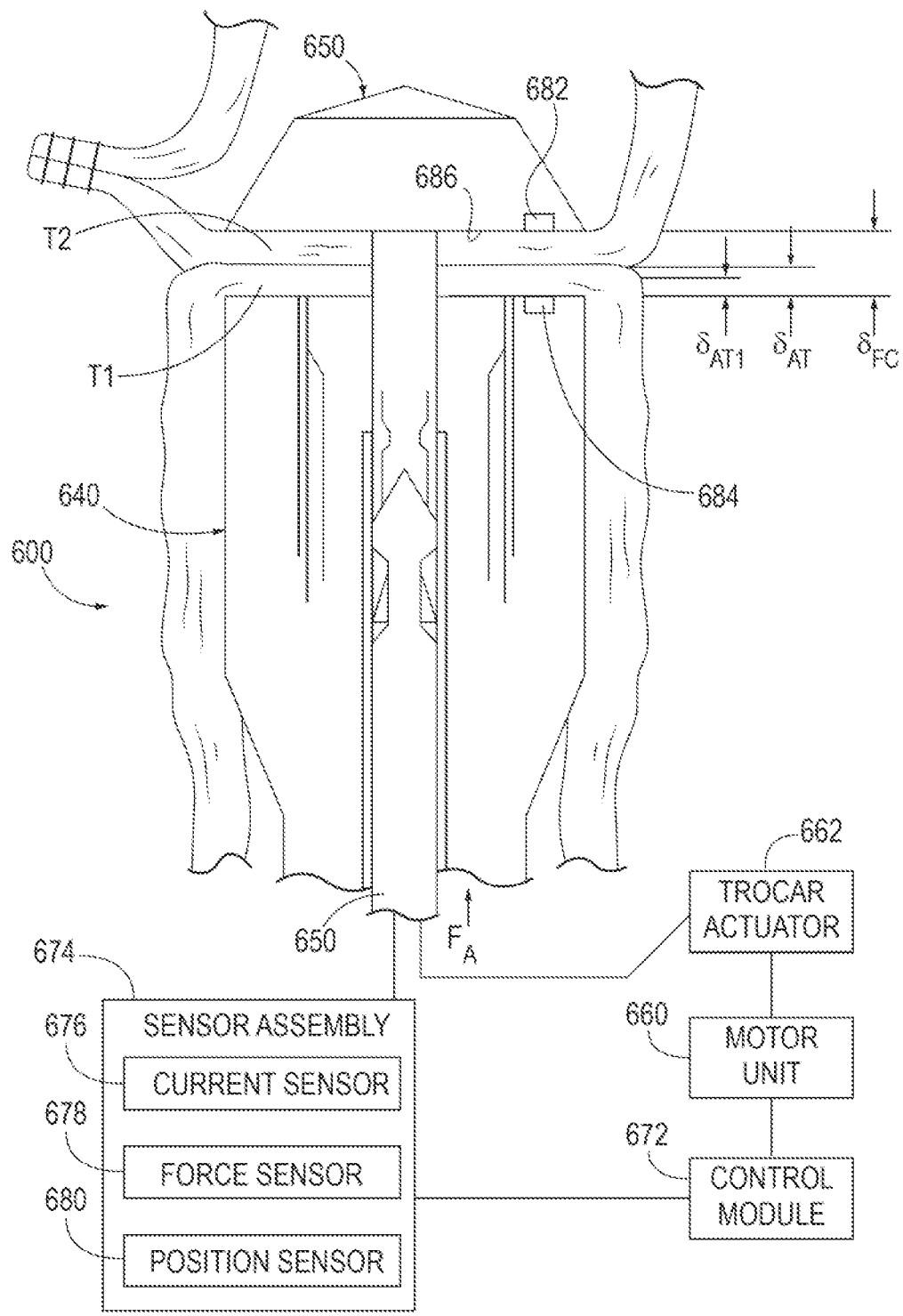
FIG. 13 depicts a schematic side cross-sectional view of the stapling head assembly and the anvil of the circular stapler of FIG. 9 operatively coupled with the control system of FIG. 10, where first and second tissue layers are disposed between the trocar and the deck surface.
Figure 14:
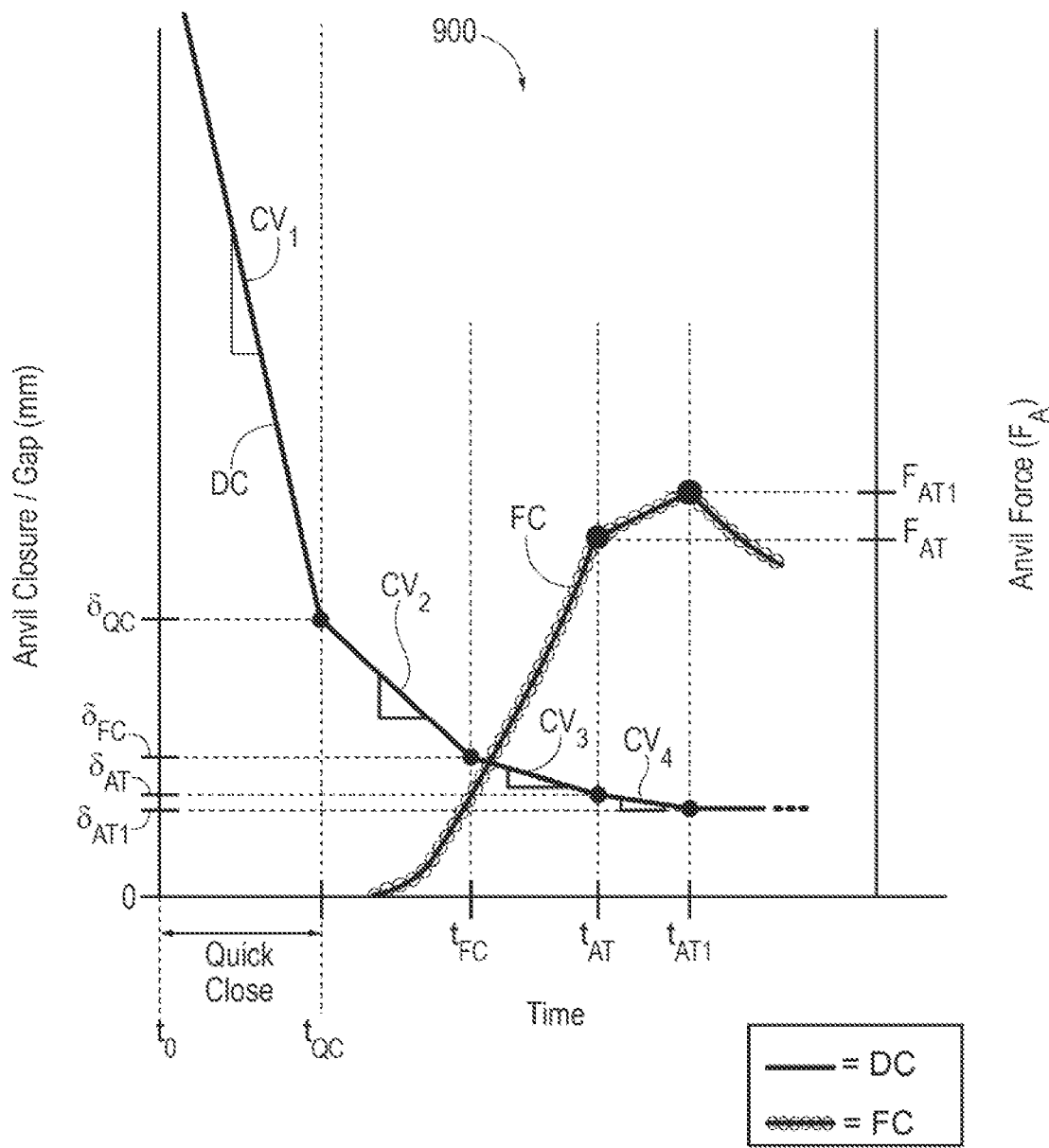
FIG. 14 depicts a line graph showing exemplary relationships between operational elements of the circular stapler of FIG. 9 over time, including anvil displacement, knife displacement, and firing load on the motor unit.

At step (806), method (800) includes sensing closure data at a first time using sensor assembly (674) as the movable member (trocar (642), anvil (650), or trocar actuator (662)) moves from the open position towards the closed position. The closure data may include one or more of an initial tissue contact position (see FIG. 13), a gap ($\delta_{QC}$, $\delta_{FC}$, $\delta_{AT}$) disposed between anvil (650) and opposing deck surface (644), or an axial force ($F_A$) on anvil (650). As shown in FIG. 13, the initial tissue contact position is defined as the position when first and second tissue layers (T1, T2) are fully approximated but not yet compressed together. In the initial tissue contact position, an initial tissue contact gap ($\delta_{FC}$) is defined between deck surface (644) or anvil (650). With further reference to FIGS. 13 and 14, gap ($\delta_{QC}$, $\delta_{FC}$, $\delta_{AT}$) shrinks as movable member moves from the open position towards the closed position. Similar to step (806) described above, method (800) also includes step (808) sensing closure data at a second time, after the first time, using sensor assembly (674) as movable member moves from the open position towards the closed position.

FIG. 13 shows a schematic side cross-sectional view of trocar (642) and anvil (650) of circular surgical stapling instrument (600) of FIG. 9 operatively coupled with control system (670) of FIG. 10, where first and second tissue layers (T1, T2) are disposed between trocar (642) and deck surface (644). As shown in FIG. 13, sensor assembly (674) may include one or more of a current sensor (676), a force sensor (678), or position sensor (680), which may be operatively coupled with motor unit (660). Sensor assembly (674) is in communication with control module (672) which is in communication with motor unit (660) to affect trocar actuator (662). Control module (672) may determine present longitudinal displacement of anvil (650) relative to deck surface (644) based on a signal provided by position sensor (680). As shown in FIG. 13, position sensor (680) may include first and second sensor portions (682, 684), where first sensor portion (682) is disposed on a proximally facing surface (686) of anvil (650) and second first sensor portion (684) is disposed on deck surface (644). As shown, proximally facing surface (686) is disposed opposite deck surface (644) and separated by gap ($\delta_{QC}$, $\delta_{FC}$, $\delta_{AT}$)

This increase in axial force ($F_A$) may be detected by one or more sensors of sensor assembly (674) in the form of current sensor (676) or force sensor (678) that communicate with control module (672) as shown in FIG. 13. For example, control module (672) may determine that axial force ($F_A$) on anvil (650) has changed based on the closure data provided by force sensor (678) that indicates an increase in axial force ($F_A$) exerted on trocar actuator (662) (and thus also anvil (650) and trocar (642)). Similarly, this axial force ($F_A$) may be exerted on trocar actuator (662) (and thus also anvil (650) and trocar (642)), or may be an electrical current drawn by motor unit (660) while actuating trocar actuator (662). The axial force ($F_A$) on anvil (650) is proportional to the electrical current drawn by motor unit (660) in moving from the open position to the closed position. It will be understood that the closure of anvil (650) against a structure induces a longitudinal extension force in anvil (650), trocar (642), and trocar actuator (662) that makes further proximal retraction of these closure components by motor unit (660) more difficult, thus increasing the electrical current force of motor unit (660). As a result, control module (672) may determine that axial force ($F_A$) on anvil (650) has increased based on the closure data provided by current sensor (676) that indicates an increase in electrical current drawn by motor unit (660).

FIG. 14 shows a line graph (900) of an exemplary closure of trocar actuator (662) (and thus trocar (642) and anvil (650)) according to method (800) described above. For the closure displacement curve (DC), the X-axis of graph (900) represents time and the Y-axis of graph (900) represents an anvil closure gap ($\delta$), as interpreted by control module (672). For the displacement curve (DC), a predetermined gap may be a quick close gap ($\delta_{QC}$) that has a higher first closure velocity (CV') than at first tissue closure gap ($\delta_{fc}$) as shown by second closure velocity ($CV_2$). Closure velocities ($CV_1$, $CV_2$, $CV_3$, $CV_4$) are measured as the change (i.e. slope) of displacement curve (DC). As shown in FIG. 14, gap ($\delta_{QC}$, $\delta_{FC}$, $\delta_{AT}$) formed between anvil (650) and opposing deck surface (644) decreases as movable member (trocar (642), anvil (650), trocar actuator (662)) moves from the open position towards the closed position (shown by gap ($\delta_{AT1}$)).

For the closure force curve (FC), the X-axis of graph (900) represents time and the Y-axis of graph (900) represents an anvil force ($F_A$), as interpreted by control module (672). The closure displacement curve (DC) and the closure force curve (FC) are superimposed on top of each other to show the relevant relationships at various times, such as at an initial time ($t_o$), a quick close time ($t_{QC}$), a partially closed time ($t_{AT}$), and a fully closed time ($t_{AT1}$). As shown, axial force ($F_A$) on anvil (650) increases once tissue is contacted. There is not a significant force ($F_A$) exerted on anvil (650) in the quick close region as first and second tissue layers (T1, T2) are not being actively compressed together. The increase in the closure force curve (FC) between quick close time ($t_{QC}$) and initial tissue contact time ($t_{FC}$) is caused by first and second tissue layers (T1, T2) being fully approximated. The axial force ($F_A$) on anvil (650) peaks at near fully closed time ($t_{AT1}$), and then decreases thereafter.

At step (810), method (800) also includes communicating closure data of sensor assembly (674) to control module (672). At step (812), control module (672) compares the current longitudinal displacement of the monitored movable member observed by control module (672), via sensor assembly (674), to the closure rate and closure stroke stored by control module (672). Control module (672) determines at step (812) whether there is a difference between the present closure rate and closure stroke and the closure rate and closure stroke obtained using the closure data. If the values are equal or within a predetermined acceptable range of one another such that there is no significant difference, control module (672) proceeds to step (814) to continues to execute the current algorithm in response to user actuations of closure trigger (624) and firing trigger (626), for example as outlined above in the steps of method (700).

Alternatively, if control module (672) determines that there is a significant difference between the values, control module (672) proceeds to step (816) to adjust the closure rate to an adjusted closure rate and the closure stroke to an adjusted closure stroke based on the determined difference. The adjusted closure rate is the speed at which the gap between anvil (650) and opposing deck surface (644) shrinks moving toward the closed position. The adjusted closure stroke is longitudinal distance between anvil (650) and opposing deck surface (644) between the open and closed positions. Adjusting the closure rate and or closure stroke may improve compression of first and second tissue layers (T1, T2) relative to a user selected staple size.

At step (818), method (800) also includes controlling motor unit (660) by executing at least one of the adjusted closure rate or the adjusted closure stroke based on determination of control module (672). Alternatively, control unit (672) may control motor unit (660) using each of the adjusted closure rate and the adjusted closure stroke based on the determination of control module (672). At step (820), method (800) includes determining with control module (672) whether the movable member has reached the closed position. If yes, method (800) may move to step (822) where the algorithm may be terminated once the closed position is reached with using the adjusted closure rate and/or adjusted closure stroke. If no, method (800) may loop back to sense closure data at additional times as discussed above with reference to steps (806, 808), such that method (800) continues.

The combined sensing of first tissue contact position, gap demonstrating anvil position, and axial force ($F_A$) improves closure rate and/or closure stroke in instrument (600) to reduce collateral damage and improve compression relative to the user's selection of staple size, thereby improving the anastomosis. Additionally, sensing the first tissue contact position, anvil position tissue gap, and axial force ($F_A$) as a means for adjusting the closure rate and/or the closure stroke may increase reliability, minimize collateral damage, and improve hemostasis.

B. Adjusting Stapling and/or Knife Algorithms Based on Closure Rate and/or Closure Stroke In addition to controlling the longitudinal displacement of trocar actuator (662) during the anvil closure stroke, control module (672) may control the longitudinal displacement of staple actuator (664) during the stapling stroke and the longitudinal displacement of knife actuator (666) during the cutting stroke based on the tissue gap user input. In particular, control module (672) may tailor the longitudinal displacements of each actuator (662, 664, 666) to ensure that actuators (662, 664, 666) are actuated longitudinally by the appropriate amount to provide a full stapling member actuation stroke and a full knife member actuation stroke without under-actuation or over-actuation relative to the target tissue gap.

In that regard, it will be appreciated that calibration of the longitudinal strokes of staple actuator (664) and knife actuator (666) may be desirable to ensure that staple actuator (664) and knife actuator (666) are actuated by the appropriate amount during a surgical procedure. Moreover, it may be beneficial to use the closure data obtained during the movable member actuation algorithm to affect the staple member actuation algorithm and the knife member actuation algorithm. As such, the corresponding staple member actuation algorithm and knife member actuation algorithm may be adjusted appropriately based on the adjustments made to the movable member actuation algorithm via method (800). Alternatively, the staple member actuation algorithm and knife member actuation algorithm may be adjusted independently of the movable member actuation algorithm.

With trocar (642) in the closed position, control unit (672) may control motor unit (660) to initiate an adjusted actuation of staple driver member to drive staples into clamped tissue. In some versions, the staple member actuation algorithm and the knife member actuation algorithm may be adjusted in a similar manner based on the same difference value determined by control module (672) in connection with actuation of the monitored movable member. It will be understood that calibration of all three actuation algorithms ensures precise longitudinal actuation of anvil (650), the staple driver member, and the knife member of instrument (600). The movable member (e.g. trocar (642), anvil (650), or trocar actuator (662)), staple driver member, and knife member are operatively coupled with motor unit (660) and are actuatable independently of one another by motor unit (660).

After executing the adjusted closure rate and/or closure stroke, method (800) may include actuating a staple driver member (not shown but similar to staple driver member (350)) to drive staples into clamped first and second tissue layers (T1, T2) using the adjusted closure rate and/or closure stroke. For example, the staple driver member may be actuated according to a staple closure stroke, a staple closure rate, and a staple pause sequence using staple actuator (664) that incorporates the adjusted closure stroke and the initial tissue contact position as described above.

Similarly, method (800) may also include actuating a knife member (not shown but similar to knife member (340)) to cut clamped tissue using the adjusted closure rate and/or closure stroke. For example, control module (672) may control motor unit (660) to initiate an adjusted actuation of knife member to cut clamped tissue in response to both initial tissue contact position ($\delta_{FC}$) and gap formed between anvil (650) and opposing deck surface (644). More specifically, knife member may be actuated according to a knife closure stroke, a knife closure rate, and a knife pause sequence that incorporates adjusted closure stroke and initial tissue contact position ($\delta_{FC}$). Alternatively, knife member may be actuated according to a knife closure stroke, a knife closure rate, and a knife pause sequence that incorporates adjusted closure stroke, initial tissue contact position ($\delta_{FC}$), as well as the staple closure stroke, the staple closure rate, and the staple pause sequence described above. As a result, knife member actuation algorithm would take into account both the movable member actuation algorithm and the staple member actuation algorithm.

Step (816) may include control module (672) controlling motor unit (660) to adjust each of adjusted closure rate, adjusted closure stroke, and a closure pause based on closure data of sensor assembly (674) communicated to control module (672), where closure pause is a time period when anvil (650) and opposing deck surface (644) do not move toward the closed position. In other words, closure stroke, closure rate, and closure pauses may be incorporated into knife member and the staple member actuation algorithm based on closure stroke and the first contact tissue position.

It will be appreciated that the actuation rates of one or more actuators (662, 664, 666) may be controlled based on additional factors as well, such as a size of stapling head assembly (640) or a target tissue gap specified by a user via user interface (616). By way of example only, control module (672) may decrease the actuation rates of one or more actuators (662, 664, 666) in the presence of a stapling head assembly of a relatively larger diameter; and increase the actuation rates of one or more actuators (662, 664, 666) in the presence of a stapling head assembly (640) of a relatively smaller diameter. Additionally, control module (672) may decrease the actuation rates of one or more actuators (662, 664, 666) for larger tissue gaps and increase the actuation rates of one or more actuators (662, 664, 666) for smaller tissue gaps, as described in greater detail above.

C. Second Exemplary Method to Adjust Closure Rate

Figure 15A:
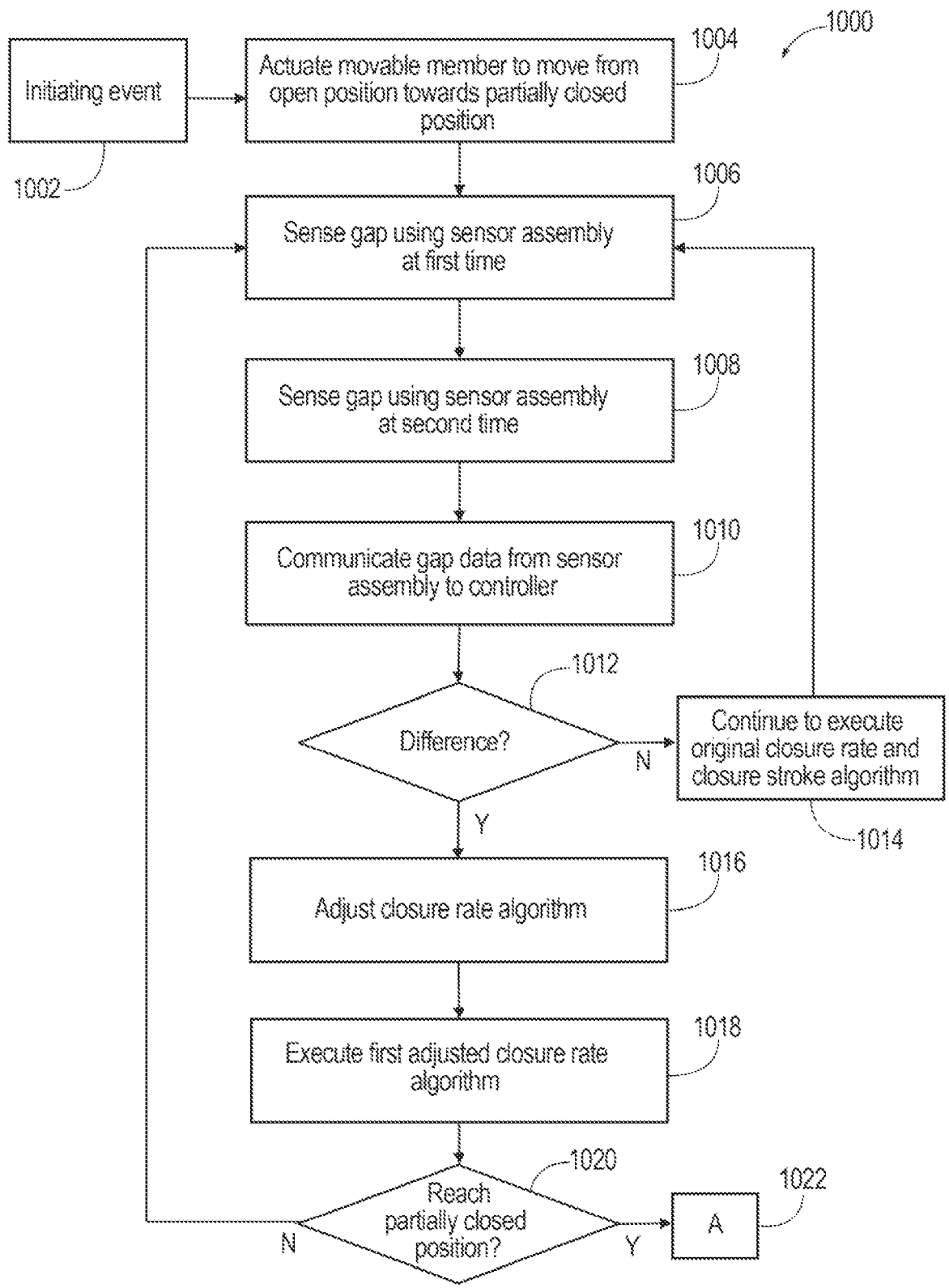
FIG. 15A depicts a diagrammatic view of a first portion of another exemplary method for controlling the circular stapler of FIG. 9 by adjusting actuation algorithms executed by the control system of FIG. 10.
Figure 15B:
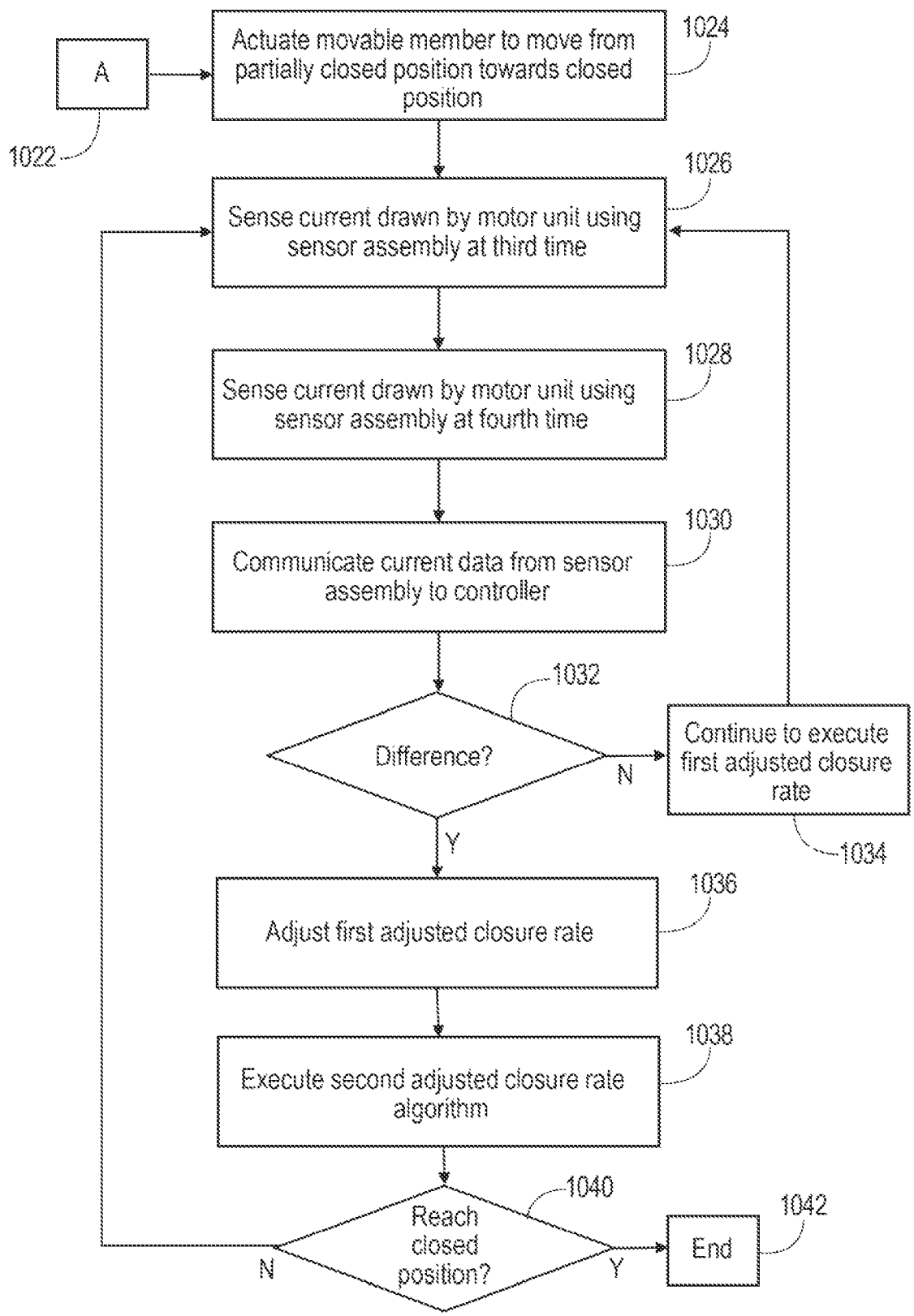
FIG. 15B depicts a diagrammatic view of a second portion of the exemplary method for controlling the circular stapler of FIG. 15A.

A second exemplary method (1000) of operating a powered surgical stapler, such as circular surgical stapling instrument (600), is shown and described with reference to FIGS. 15A-15B. Particularly, FIGS. 15A-15B show diagrammatic views of method (1000) for calibrating a closure rate of a movable member of circular stapler of FIG. 9 by adjusting actuation algorithms executed by the control system (670) of FIG. 10. FIG. 15A shows a first portion of method (1000) and FIG. 15B shows a second portion of method (1000). According to method (1000), anvil closure rate varies based on a gap remaining when sensing the initial tissue contact position and varies closure rate based on rate of current increased sensed by motor unit (660) closing anvil (650) using trocar actuator (662). Trocar (642) is actuatable between an open position for receiving at least first and second tissue layers (T1, T2), a partially closed position, and the closed position, where at least first and second tissue layers (T1, T2) are compressed together.

As shown in FIG. 15A, method (1000) begins at step (1002) with an initiating event, which may be an actuation of closure trigger (624) following attachment of anvil (650) to trocar (642) during a surgical procedure. In response to the initiating event, control module (672) executes the stored movable member actuation algorithm at step (1004) to activate motor unit (660) to actuate trocar actuator (662) proximally to transition anvil (650) toward the closed state. At step (1004), method (1000) includes control module (672) controlling motor unit (660) to actuate trocar (642) to move anvil (650) from the open position towards the partially closed position. Prior to or during execution of the movable member actuation algorithm, control module (672) determines that a monitored movable member (one of trocar actuator (662), trocar (642), or anvil (650)) is in a predetermined position, e.g. via detection by sensor assembly (674), for example using position sensor (680). By way of example only, the predetermined position may correspond to anvil (650) in a fully open state.

At step (1006), method (1000) includes sensing a gap formed between anvil (650) and opposing deck surface (644) as trocar (642) moves from the open position towards the partially closed position at a first time using position sensor (680) of sensor assembly (674). The partially closed position may be a predetermined position (e.g. quick close gap ($\delta_{QC}$)) or the initial tissue contact position shown in FIG. 13. As shown, the initial tissue contact position is defined as the position when first and second tissue layers (T1, T2) are fully approximated but not yet compressed together. In the initial tissue contact position, initial tissue contact gap ($\delta_{FC}$) is defined between deck surface (644) or anvil (650). With further reference to FIGS. 13 and 14, gap ($\delta_{QC}$, $\delta_{FC}$) shrinks as movable member moves from the open position towards the partially closed position. Similar to step (1006), method (1000) also includes step (1008) sensing the gap formed between anvil (650) and opposing deck surface (644) using position sensor (680) of sensor assembly (674) at a second time, after the first time, using sensor assembly (674) as the movable member moves from the open position towards the closed position.

Position sensor (680) of sensor assembly (674) is in communication with control module (672), which is in communication with motor unit (660) to affect trocar actuator (662). Control module (672) may determine present longitudinal displacement of anvil (650) relative to deck surface (644) based on a signal provided by position sensor (680). As shown in FIG. 13, position sensor (680) includes first and second sensor portions (682, 684), where first sensor portion (682) is disposed on anvil (650) and second sensor portion (684) is disposed on deck surface (644). At step (1010), method (1000) also includes communicating gap data obtained from position sensor (680) of sensor assembly (674) to control module (672).

At step (1012), control module (672) compares the current closure rate of the monitored movable member observed by control module (672), via position sensor (680), to the closure rate stored by control module (672). Control module (672) determines at step (1012) whether there is a difference between the present closure rate and the closure rate obtained using gap data. If the values are equal or within a predetermined acceptable range of one another such that there is no significant difference, control module (672) proceeds to step (1014) to continues to execute the current algorithm in response to user actuations of closure trigger (624) and firing trigger (626). Method (800) may loop back to sense gap data at respective times as discussed above with reference to steps (1006, 1008), such that method (1000) continues.

Alternatively, if control module (672) determines that there is a significant difference between the values, control module (672) proceeds to step (1016) to adjust the closure rate to a first adjusted closure rate based on the determined difference. The first adjusted closure rate is speed at which gap ($\delta_{QC}$, $\delta_{FC}$) formed between anvil (650) and opposing deck surface (644) shrinks moving toward the partially closed position. In other words at step (1016), method (1000) also includes controlling motor unit (660) to adjust the closure rate based on gap data from sensor assembly (674) communicated to control module (672) as trocar (642) is moved from the open position to the partially closed position. Adjusting the closure rate may improve compression of first and second tissue layers (T1, T2) relative to a user selected staple size. It is also envisioned that the closure stroke may be adjusted using the gap data, in a similar manner to adjusting the closure rate to the first adjusted closure rate.

At step (1020), method (800) includes determining with control module (672) whether the movable member has reached the partially closed position. The partially closed position may be a predetermined position (e.g. quick close gap ($\delta_{QC}$)) or the initial tissue contact position shown in FIG. 13. If yes, method (800) may move to step (1022) of FIG. 15B once the partially closed position is reached with using the adjusted closure rate. This determination may be based on the gap data obtained from position sensor (680).

At step (1024), method (1000) includes control module (672) controlling motor unit (660) to actuate trocar (642) to move anvil (650) from the partially closed position towards the closed position. At step (1026), method (1000) also includes sensing current data at a third time using sensor assembly (674), where current data includes current drawn by motor unit (660) as trocar (642) is moved from the partially closed position to the closed position ($\delta_{AT1}$). Similarly, at step (1028), method (1000) also includes sensing current data at a fourth time using sensor assembly (674), where current data includes current drawn by motor unit (660) as trocar (642) is moved from the partially closed position to the closed position ($\delta_{AT1}$). The closure of anvil (650) against a structure induces a longitudinal extension force in anvil (650), trocar (642), and trocar actuator (662) that makes further proximal retraction of these closure components by motor unit (660) more difficult, thus increasing the electrical current force of motor unit (660). As a result, the first adjusted closure rate may be increased or decreased in response to detection by current sensor (676) of the increase in electrical current drawn by motor unit (660).

This increase in axial force ($F_A$) may be detected by one or more sensors of sensor assembly (674) in the form of current sensor (676) or force sensor (678) that communicate with control module (672) as shown in FIG. 13. Axial force ($F_A$) may be exerted on trocar actuator (662) (and thus also anvil (650) and trocar (642)), or may be an electrical current drawn by motor unit (660) while actuating trocar actuator (662). Control module (672) may determine that axial force ($F_A$) on anvil (650) has changed based on the current data provided by force sensor (678) that indicates an increase in axial force ($F_A$) exerted on trocar actuator (662) (and thus also anvil (650) and trocar (642)). The axial force ($F_A$) on anvil (650) is proportional to electrical current drawn by motor unit (660) in moving from the open position to the closed position. As a result, force sensor (678) may also produce the current data. At step (1030), method (1000) also includes communicating the current data obtained from sensor assembly (674) (e.g. current sensor (676) or force sensor (678)) to control module (672).

At step (1032), control module (672) compares the closure rate observed by control module (672) using current sensor (676) or force sensor (678), to the first adjusted closure rate stored by control module (672). Control module (672) determines at step (1032) whether there is a difference between the closure rate obtained using current data and the present closure rate (e.g. first adjusted closure rate). If the values are equal or within a predetermined acceptable range of one another such that there is no significant difference, control module (672) proceeds to step (1034) to continue to execute the first adjusted closure rate.

Alternatively, if control module (672) determines that there is a significant difference between the values, control module (672) proceeds to step (1036) to adjust the first adjusted closure rate to the second adjusted closure rate based on the determined difference. The second adjusted closure rate is the speed at which the gap formed between anvil (650) and opposing deck surface (644) shrinks moving toward the closed position (shown by closed gap $\delta_{AT1}$)). Adjusting the first adjusted closure rate to the second adjusted closure rate may improve compression of first and second tissue layers (T1, T2) relative to a user selected staple size.

At step (1038), method (1000) also includes controlling motor unit (660) using the second adjusted closure rate based on determination of control module (672). At step (1040), method (1000) includes determining with control module (672) whether the movable member (e.g. trocar (642), anvil (650), or trocar actuator (662)) has reached the closed position. If yes, method (1000) may move to step (1042) where the algorithm may be terminated once the closed position is reached with using the adjusted closure rate. If no, method (1000) may loop back to sense current data at respective times as discussed above with reference to steps (1026, 1028), such that method (1000) continues.

As previously discussed, it may be beneficial to use one or more of the first and second adjusted closure rates obtained during the movable member actuation algorithm, to affect the staple member actuation algorithm and the knife member actuation algorithm. As such, the corresponding staple member actuation algorithm and knife member actuation algorithm may be adjusted appropriately based on the adjustments made to the movable member actuation algorithm via method (1000). Alternatively, the staple member actuation algorithm and knife member actuation algorithm may be adjusted independently of the movable member actuation algorithm.

IV. EXEMPLARY COMBINATIONS

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of operating a powered surgical stapler that includes a motor unit, at least one movable member operatively coupled with the motor unit, a controller in communication with the motor unit, a sensor assembly in communication with the controller, an anvil, and an opposing deck surface, wherein the movable member is actuatable between an open position for receiving at least first and second layers of tissue and a closed position where the at least first and second layers of tissue are compressed together, the method comprising: (a) controlling the motor unit to actuate the movable member to move from the open position towards the closed position; (b) sensing closure data using the sensor assembly, wherein the closure data includes each of: (i) an initial tissue contact position, (ii) a gap formed between the anvil and the opposing deck surface as the movable member moves from the open position towards the closed position, and (iii) an axial force on the anvil as the movable member moves from the open position towards the closed position; (c) communicating the closure data of the sensor assembly to the controller; (d) determining with the controller at least one of an adjusted closure rate or an adjusted closure stroke using the closure data; and (e) controlling the motor unit using at least one of the adjusted closure rate or the adjusted closure stroke based on the determination of the controller.

Example 2

The method of Example 1, wherein the adjusted closure rate is the speed at which the gap between the anvil and the opposing deck surface shrinks moving toward the closed position, wherein the adjusted closure stroke is the longitudinal distance between the anvil and the opposing deck surface between the open and closed positions.

Example 3

The method of any of the preceding Examples, wherein the initial tissue contact position is the position when the at least first and second layers of tissue are fully approximated but not yet compressed together.

Example 4

The method of any of the preceding Examples, wherein the at least one movable member comprises a trocar actuator, a trocar, or the anvil.

Example 5

The method of any of the preceding Examples, wherein the at least one movable member further comprises a staple driver member, wherein the at least one movable member further comprises a knife member, wherein the method further comprises: (a) with the moveable member in the closed position, controlling the motor unit to initiate an adjusted actuation of the staple driver member to drive staples into the clamped tissue in response to the both the initial tissue contact position and the gap formed between the anvil and the opposing deck surface; and (b) controlling the motor unit to initiate an adjusted actuation of the knife member to cut the clamped tissue in response to the both the initial tissue contact position and the gap formed between the anvil and the opposing deck surface.

Example 6

The method of any of the preceding Examples, wherein determining with the controller at least one of the adjusted closure rate or the adjusted closure stroke using the closure data further comprises determining with the controller the adjusted closure rate and the adjusted closure stroke using the closure data, wherein controlling the motor unit using at least one of the adjusted closure rate or the adjusted closure stroke based on the determination of the controller further comprises determining with the controller the adjusted closure rate and the adjusted closure stroke using the closure data.

Example 7

The method of Example 6, wherein controlling the motor unit to adjust each of the closure rate and the closure stroke further comprises controlling the motor unit to adjust each of the adjusted closure rate, the adjusted closure stroke, and a closure pause based on the closure data of the sensor assembly communicated to the controller, wherein the closure pause is a time period when the anvil and the opposing deck surface do not move toward the closed position.

Example 8

The method of any of Examples 1 through 4 and Examples 6 through 7, further comprising: (a) actuating the movable member to clamp tissue using at least one of the adjusted closure rate or the adjusted closure stroke; (b) actuating a staple driver member to drive staples into the clamped tissue; and (c) actuating a knife member to cut the clamped tissue.

Example 9

The method of Example 8, wherein the closure member, the staple driver member, and the knife member are operatively coupled with the motor unit and are actuatable independently of one another by the motor unit.

Example 10

The method of any of Examples 8 through 9, wherein actuating the staple driver member further comprises actuating the staple driver member according to a staple closure stroke, a staple closure rate, and a staple pause sequence that incorporates the adjusted closure stroke and the initial tissue contact position, wherein actuating the knife member further comprises actuating the knife member according to a knife closure stroke, a knife closure rate, and a knife pause sequence that incorporates the adjusted closure stroke and the initial tissue contact position.

Example 11

The method of Example 10, wherein actuating the knife member further comprises actuating the knife member according to the knife closure stroke, the knife closure rate, and the knife pause sequence that incorporates the adjusted closure stroke, the initial tissue contact position, the staple closure stroke, the staple closure rate, and the staple pause sequence.

Example 12

The method of any of the preceding Examples, wherein the sensor assembly comprises a force sensor operatively coupled with the one of the anvil or the trocar, wherein the method further comprises determining with the controller that the axial force on the anvil has changed based on the closure data provided by the force sensor that indicates an increase in longitudinal force exerted on the movable member.

Example 13

The method of any of the preceding Examples, wherein the sensor assembly comprises a current sensor operatively coupled with the motor unit, wherein the method further comprises determining with the controller that the axial force on the anvil has increased based on the closure data provided by the current sensor that indicates an increase in electrical current drawn by the motor unit.

Example 14

The method of any of the preceding Examples, wherein controlling the motor unit using at least one of the adjusted closure rate or the adjusted closure stroke further comprises decreasing the adjusted closure rate or the adjusted closure stroke in response to detection by the current sensor of an increase in the electrical current drawn by the motor unit

Example 15

The method of any of the preceding Examples, wherein the sensor assembly comprises a position sensor operatively coupled with at least one of the anvil or the trocar, wherein the method further comprises determining with the controller the actual longitudinal displacement of the anvil relative to the deck surface based on the closure data provided by the position sensor.

Example 16

A method of operating a powered surgical stapler that includes a motor unit, at least one movable member operatively coupled with the motor unit, a controller in communication with the motor unit, and a sensor assembly in communication with the controller, an anvil, and an opposing deck surface, wherein the movable member is actuatable between an open position for receiving at least first and second layers of tissue and a closed position where the at least first and second layers of tissue are compressed together, the method comprising: (a) controlling the motor unit to actuate the movable member to move from the open position towards the closed position; (b) sensing closure data using the sensor assembly, wherein the closure data includes at least one of: (i) an initial tissue contact position defined by when the at least first and second layers of tissue are approximated but not yet compressed together, (ii) a gap formed between the anvil and the opposing deck surface as the movable member moves from the open position towards the closed position, and (iii) an axial force on the anvil as the movable member moves from the open position towards the closed position; (c) communicating the closure data of the sensor assembly to the controller; (d) determining with the controller an adjusted closure rate and an adjusted closure stroke using the closure data; and (e) controlling the motor unit using the adjusted closure rate and the adjusted closure stroke based on the determination of the controller, wherein the adjusted closure rate is the speed at which the gap formed between the anvil and the opposing deck surface move toward the closed position, wherein the adjusted closure stroke is the longitudinal distance between the anvil and the opposing deck surface between the open and closed positions.

Example 17

The method of Example 16, wherein the closure data includes each of: the initial tissue contact position, the position of the anvil relative to the opposing deck surface, and the axial force on the anvil.

Example 18

The method of any of Examples 16 through 17, further comprising: (a) actuating the movable member to clamp tissue using at least one of the adjusted closure rate or the adjusted closure stroke; (b) actuating a staple driver member to drive staples into the clamped tissue; and (c) actuating a knife member to cut the clamped tissue, wherein actuating the staple driver member further comprises actuating the staple driver member according to a staple closure stroke, a staple closure rate, and a staple pause sequence that incorporates the adjusted closure stroke and the initial tissue contact position, wherein actuating the knife member further comprises actuating the knife member according to a knife closure stroke, a knife closure rate, and a knife pause sequence that incorporates the adjusted closure stroke and the initial tissue contact position.

Example 19

A method of operating a powered surgical stapler that includes a motor unit, at least one movable member operatively coupled with the motor unit, a controller in communication with the motor unit, a sensor assembly in communication with the controller, an anvil operatively coupled with the movable member, and an opposing deck surface, wherein the movable member is actuatable between an open position for receiving at least first and second layers of tissue, a partially closed position, and a closed position where the at least first and second layers of tissue are compressed together, the method comprising: (a) controlling the motor unit to actuate the movable member to move from the open position towards the partially closed position; (b) sensing gap data using the sensor assembly, wherein the gap data includes a gap formed between the anvil and the opposing deck surface as the movable member moves from the open position towards the partially closed position; (c) communicating the gap data of the sensor assembly to the controller; (d) determining with the controller a first closure rate using the gap data; (e) controlling the motor unit to adjust the first closure rate based on the gap data of the sensor assembly communicated to the controller as the movable member is moved from the open position to the partially closed position, wherein the first closure rate is the speed at which a gap formed between the anvil and the opposing deck surface shrinks moving toward the partially closed position; (f) sensing current data using the sensor assembly, wherein the current data includes current drawn by the motor unit as the movable member moves from the partially closed position to the closed position; (g) communicating the current data of the sensor assembly to the controller; (h) determining with the controller a second closure rate using the current data; and (i) controlling the motor unit to adjust a second closure rate based on the current data of the sensor assembly communicated to the controller, wherein the second closure rate is the speed at which the gap formed between the anvil and the opposing deck surface shrinks moving toward the closed position.

Example 20

The method of Example 19, wherein the partially closed position is either a predetermined position or an initial tissue contact position based on a position of the anvil relative to the opposing deck surface, wherein the gap data further includes sensing the initial tissue contact position defined by when the at least first and second layers of tissue are approximated but not yet compressed together.

Example 21

A powered surgical stapler comprising: (a) a motor unit; (b) at least one movable member operatively coupled with the motor unit, wherein the movable member is configured to be actuated at least between an open position for receiving at least first and second layers of tissue and a closed position where the at least first and second layers of tissue are compressed together; (c) a sensor assembly configured to sense: (i) an initial tissue contact position, and (iii) an axial force as the movable member moves from the open position towards the closed position; and (d) a controller in communication with the motor unit and the sensor assembly, wherein the controller is configured to: (i) operate a control program, and (ii) switch to an adaptive control program when the controller determines the initial tissue contact position has been reached using data from the sensor assembly of an increase in axial force.

Example 22

The powered surgical stapler of Example 21, further comprising an anvil and an opposing deck surface, wherein the sensor assembly is configure to sense a gap formed between the anvil and the opposing deck surface as the movable member moves from the open position towards the closed position, wherein the controller is configured to switch to the adaptive control program when the controller determines the initial tissue contact position has been reached using data from the sensor assembly of the increase in the axial force and by stroke location using the gap formed between the anvil and the opposing deck surface.

Example 23

The powered surgical stapler of any one or more of Examples 21 through 22, wherein the control program includes a closure rate and a closure stroke, wherein the adaptive closure program includes at least one of an adjusted closure rate different from the closure rate or an adjusted closure stroke different from the closure stroke, wherein the controller is configured to determine at least one of an adjusted closure rate or an adjusted closure stroke using the initial tissue contact position and the axial force acquired by the sensor assembly.

Example 24

The powered surgical stapler of Example 23, wherein the controller is configured to determine each of an adjusted closure rate or an adjusted closure stroke using the initial tissue contact position and the axial force acquired by the sensor assembly.

Example 25

The powered surgical stapler of any of Examples 23 through 24, further comprising an anvil and an opposing deck surface, wherein the adjusted closure rate is the speed at which a gap between the anvil and the opposing deck surface shrinks moving toward the closed position, wherein the adjusted closure stroke is the longitudinal distance between the anvil and the opposing deck surface between the open and closed positions.

Example 26

The powered surgical stapler of any of Examples 21 through 25, wherein the initial tissue contact position is the position when the at least first and second layers of tissue are fully approximated but not yet compressed together.

Example 27

The powered surgical stapler of any of Examples 21 through 26, wherein the at least one movable member comprises a trocar actuator, a trocar, or the anvil.

Example 28

The powered surgical stapler of any of Examples 21 through 27, further comprising a staple driver member configured to drive staples into the clamped tissue, and a knife member configured to cut the clamped tissue.

Example 29

The powered surgical stapler of any of Examples 21 through 28, wherein the movable member, the staple driver member, and the knife member are operatively coupled with the motor unit and are configured to be actuated independently of one another by the motor unit.

Example 30

The powered surgical stapler of any of Examples 21 through 29, further comprising an anvil, wherein the sensor assembly comprises a force sensor operatively coupled with the one of the anvil or the trocar, wherein the controller is configured to determine that the axial force on the anvil has changed based on data provided by the force sensor that indicates an increase in longitudinal force exerted on the movable member.

Example 31

The powered surgical stapler of any of Examples 21 through 30, wherein the powered surgical stapler further comprises an anvil, wherein the sensor assembly comprises a current sensor operatively coupled with the motor unit, wherein the controller is configured to determine the axial force on the anvil has increased based on data provided by the current sensor that indicates an increase in electrical current drawn by the motor unit.

Example 32

The powered surgical stapler of any of Examples 21 through 31, wherein the powered surgical stapler further comprises an anvil, a trocar, and a deck surface, wherein the sensor assembly comprises a position sensor operatively coupled with at least one of the anvil or the trocar, wherein the controller is configured to determine actual longitudinal displacement of the anvil relative to the deck surface based on closure data provided by the position sensor.

V MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 16/574,773, entitled " Method for Calibrating Movements of Actuated Members of Powered Surgical Stapler," filed on Sep. 18, 2019, published as U.S. Pub. No. 2021/0077111 on Mar. 18, 2021, issued as U.S. Pat. No. 11,464,516 on Oct. 11, 2022; U.S. Pat. App. No. 16/574,797, entitled "Method for Controlling Cutting Member Actuation for Powered Surgical Stapler," filed on Sep. 18, 2019, published as U.S. Pub. No. 2021/0077112 on Mar. 18, 2021, issued as U.S. Pat. No. 11,123,074 on Sep. 21, 2021; and U.S. Pat. App. No. 16/574,299, entitled "Anvil Retention and Release Features for Powered Circular Surgical Stapler," filed on Sep. 18, 2019, published as U.S. Pub. No. 2021/0077093 on Mar. 18, 2021, issued as U.S. Pat. No. 11,185,324 on Nov. 30, 2021. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A powered surgical stapler comprising:
   (a) a motor unit;
   (b) at least one movable member operatively coupled with the motor unit, wherein the movable member is configured to be actuated at least between an open position for receiving at least first and second layers of tissue and a closed position for compressing the at least first and second layers of tissue together;
   (c) an anvil surface;
   (d) a deck surface;
   (e) a sensor assembly configured to sense closure data, wherein the closure data includes each of:
      (i) an initial tissue contact position,
      (ii) a gap formed between the anvil surface and the deck surface as the movable member moves from the open position towards the closed position, and
      (iii) an axial force as the movable member moves from the open position towards the closed position; and
   (f) a controller in communication with the motor unit and the sensor assembly, wherein the controller is configured to:
      (i) control the motor unit to actuate the movable member to move from the open position towards the closed position,
      (ii) receive the closure data from the sensor assembly,
      (iii) determine at least one of an adjusted closure rate or an adjusted closure stroke of the movable member using the closure data, and
      (iv) control the motor unit using at least one of the adjusted closure rate or the adjusted closure stroke.

2. The powered surgical stapler of claim 1, wherein the adjusted closure rate is the speed at which a gap between the anvil surface and the deck surface shrinks moving toward the closed position, wherein the adjusted closure stroke is the longitudinal distance between the anvil surface and the opposing deck surface between the open and closed positions.

3. The powered surgical stapler of claim 1, wherein the initial tissue contact position is the position when the at least first and second layers of tissue are fully approximated but not yet compressed together.

4. The powered surgical stapler of claim 1, wherein the at least one movable member comprises a trocar actuator, a trocar, or an anvil that includes the anvil surface.

5. The powered surgical stapler of claim 1, wherein the at least one movable member further comprises a staple driver member, wherein the at least one movable member further comprises a knife member, wherein the controller is configured to:
   (a) with the movable member in the closed position, control the motor unit to initiate an adjusted actuation of the staple driver member to drive staples into the clamped tissue in response to the both the initial tissue contact position and the gap formed between the anvil surface and the opposing deck surface, and
   (b) control the motor unit to initiate an adjusted actuation of the knife member to cut the clamped tissue in response to the both the initial tissue contact position and the gap formed between the anvil surface and the opposing deck surface.

6. The powered surgical stapler of claim 1, wherein the controller is configured to determine the adjusted closure rate and the adjusted closure stroke using the closure data, and control the motor unit using the adjusted closure rate and the adjusted closure stroke.

7. The powered surgical stapler of claim 1, wherein the controller is configured to control the motor unit to adjust each of the adjusted closure rate, the adjusted closure stroke, and a closure pause based on the closure data of the sensor assembly communicated to the controller, wherein the closure pause is a time period when the anvil surface and the opposing deck surface do not move toward the closed position.

8. The powered surgical stapler of claim 1, wherein the controller is configured to:
   (a) actuate the movable member to clamp tissue using at least one of the adjusted closure rate or the adjusted closure stroke,
   (b) actuate a staple driver member to drive staples into the clamped tissue, and
   (c) actuate a knife member to cut the clamped tissue.

9. The powered surgical stapler of claim 8, wherein the movable member, the staple driver member, and the knife member are operatively coupled with the motor unit and are actuatable independently of one another by the motor unit.

10. The powered surgical stapler of claim 9, wherein the staple driver member is actuated according to a staple closure stroke, a staple closure rate, and a staple pause sequence that incorporates the adjusted closure stroke and the initial tissue contact position, wherein the knife member is actuated according to a knife closure stroke, a knife closure rate, and a knife pause sequence that incorporates the adjusted closure stroke and the initial tissue contact position.

11. The powered surgical stapler of claim 10, wherein the knife member is actuated according to the knife closure stroke, the knife closure rate, and the knife pause sequence that incorporates the adjusted closure stroke, the initial tissue contact position, the staple closure stroke, the staple closure rate, and the staple pause sequence.

12. The powered surgical stapler of claim 1, wherein the sensor assembly comprises a force sensor operatively coupled with the one of the anvil surface or a trocar, wherein the controller is configured to determine that the axial force on the anvil has changed based on the closure data provided by the force sensor that indicates an increase in longitudinal force exerted on the movable member.

13. The powered surgical stapler of claim 1, wherein the sensor assembly comprises a current sensor operatively coupled with the motor unit, wherein the controller is configured to determine that the axial force on the anvil surface has increased based on the closure data provided by the current sensor that indicates an increase in electrical current drawn by the motor unit.

14. The powered surgical stapler of claim 13, wherein the controller is configured to control the motor unit by decreasing the adjusted closure rate or the adjusted closure stroke in response to detection by the current sensor of the increase in the electrical current drawn by the motor unit.

15. The powered surgical stapler of claim 1, wherein the sensor assembly comprises a position sensor operatively coupled with at least one of a trocar or an anvil that includes the anvil surface, wherein the controller is configured to determine the actual longitudinal displacement of the anvil surface relative to the deck surface based on the closure data provided by the position sensor.

16. A powered surgical stapler comprising:
(a) a motor unit;
(b) at least one movable member operatively coupled with the motor unit, wherein the movable member is configured to be actuated at least between an open position for receiving at least first and second layers of tissue and a closed position for compressing the at least first and second layers of tissue together;
(c) an anvil surface;
(d) a deck surface;
(e) a sensor assembly configured to sense closure data, wherein the closure data includes at least one of:
  (i) an initial tissue contact position defined by when the at least first and second layers of tissue are approximated but not yet compressed together,
  (ii) a gap formed between the anvil surface and the opposing deck surface as the movable member moves from the open position towards the closed position, and
  (iii) an axial force on the anvil surface as the movable member moves from the open position towards the closed position; and
(f) a controller in communication with the motor unit and the sensor assembly, wherein the controller is configured to:
  (i) control the motor unit to actuate the movable member to move from the open position towards the closed position,
  (ii) receive the closure data of the sensor assembly,
  (iii) determine an adjusted closure rate and an adjusted closure stroke of the movable member using the closure data, and
  (iv) control the motor unit using the adjusted closure rate and the adjusted closure stroke, wherein the adjusted closure rate is the speed at which the gap formed between the anvil surface and the opposing deck surface decreases in size as the movable member moves toward the closed position, wherein the adjusted closure stroke is the longitudinal distance traveled by the movable member as the moveable member moves between the anvil surface and the opposing deck surface between the open and closed positions.

17. The powered surgical stapler of claim 16, wherein the closure data includes at least two of the initial tissue contact position, the gap, and the axial force.

18. The powered surgical stapler of claim 16, wherein the closure data includes each of the initial tissue contact position, the gap, and the axial force.

19. The powered surgical stapler of claim 16, wherein the movable member, a staple driver member, and a knife member are operatively coupled with the motor unit and are configured to be actuated independently of one another by the motor unit.

20. A powered surgical stapler comprising:
(a) a motor unit;
(b) at least one movable member operatively coupled with the motor unit, wherein the movable member is configured to be actuated at least between an open position for receiving at least first and second layers of tissue and a closed position for compressing the at least first and second layers of tissue together;
(c) an anvil that includes staple forming pockets;
(d) a deck surface that opposes the staple forming pockets of the anvil;
(e) a sensor assembly configured to sense:
  (i) an initial tissue contact position at which the anvil first contacts the first or second layer of tissue, and
  (ii) an axial force as the movable member moves from the open position towards the closed position; and
(f) a controller in communication with the motor unit and the sensor assembly, wherein the controller is configured to:
  (i) operate a control program that includes a closure rate and a closure stroke for the movable member,
  (ii) determine that the initial tissue contact position has been reached using data from the sensor assembly indicating an increase in the axial force, and
  (iii) based on the determination, activate at least one of an adjusted closure rate different from the closure rate or an adjusted closure stroke of the movable member different from the closure stroke.

* * * * *